(12) United States Patent
Kubo

(10) Patent No.: US 9,107,268 B2
(45) Date of Patent: Aug. 11, 2015

(54) CALIBRATION METHOD AND ENDOSCOPE SYSTEM

(71) Applicant: FUJIFILM Corporation, Tokyo (JP)

(72) Inventor: Masahiro Kubo, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/500,265

(22) Filed: Sep. 29, 2014

(65) Prior Publication Data

US 2015/0091447 A1 Apr. 2, 2015

(30) Foreign Application Priority Data

Sep. 30, 2013 (JP) ................................. 2013-204301

(51) Int. Cl.
*H05B 37/02* (2006.01)
*H05B 33/08* (2006.01)
*A61B 1/00* (2006.01)

(52) U.S. Cl.
CPC ........ *H05B 33/0869* (2013.01); *A61B 1/00057* (2013.01); *H05B 33/0848* (2013.01)

(58) Field of Classification Search
CPC .... H05B 37/02; H05B 33/08; H05B 33/0833; H05B 33/0842; H05B 33/0845; A61B 1/00057; A61B 1/06; A61B 1/0661
USPC .......................... 315/149–153, 291, 307, 308
See application file for complete search history.

(56) References Cited

U.S. PATENT DOCUMENTS

| 7,018,331 B2 * | 3/2006 | Chang et al. ................... 600/182 |
| 2011/0050107 A1 | 3/2011 | Yoshida et al. |
| 2012/0206050 A1 * | 8/2012 | Spero ............................ 315/152 |

FOREIGN PATENT DOCUMENTS

| EP | 2 452 611 A1 | 5/2012 |
| JP | 4694285 B2 | 6/2011 |

OTHER PUBLICATIONS

Partial European Search Report dated Feb. 24, 2015, issued in corresponding European Patent Application No. 14186757.2.

* cited by examiner

*Primary Examiner* — Jimmy Vu
(74) *Attorney, Agent, or Firm* — Birch, Stewart, Kolasch & Birch, LLP

(57) ABSTRACT

Light from each LED is applied to an integrating sphere (reference object), and a light amount calculator calculates light reflected from the integrating sphere. Calibration data, in which source control signals applied to the LEDs are associated with amounts of the light from the LEDs emitted in response to the source control signals, respectively, is generated. A maximum amount of the light from each LED is set in accordance with a predetermined light amount ratio. Based on the maximum light amount, an nth light amount which corresponds to a brightness step n is set. With reference to the calibration data, the source control signal which corresponds to the nth light amount is set as the source control signal for the brightness step n. A light control table is generated by associating the source control signal for the brightness step n with a brightness command signal for the brightness step n.

14 Claims, 18 Drawing Sheets

FIG. 4

|  | B-LED | G-LED | R-LED | FIRST SPECIAL LIGHT LED | SECOND SPECIAL LIGHT LED | THIRD SPECIAL LIGHT LED |
|---|---|---|---|---|---|---|
| NORMAL MODE | ON | ON | ON | ON | ON | OFF |
| FIRST SPECIAL MODE | OFF | ON | OFF | ON | ON | OFF |
| SECOND SPECIAL MODE | OFF | ON | ON | ON | ON | OFF |
| THIRD SPECIAL MODE | OFF | OFF | OFF | OFF | ON | ON |

FIG. 5

|  | SET LIGHT AMOUNT RATIO |
|---|---|
| NORMAL MODE | X1 (LB1 IS THE HIGHEST, LSA1=LB1×w1%, LSA2=LB1×w2%) |
| FIRST SPECIAL MODE | X2 (LSA2 IS THE HIGHEST, LSB2=LSA2×t1%) |
| SECOND SPECIAL MODE | X3 (LSA3 IS THE HIGHEST, LSB3=LSA3×t2%) |
| THIRD SPECIAL MODE | X4 (LSC4>LSB4) |

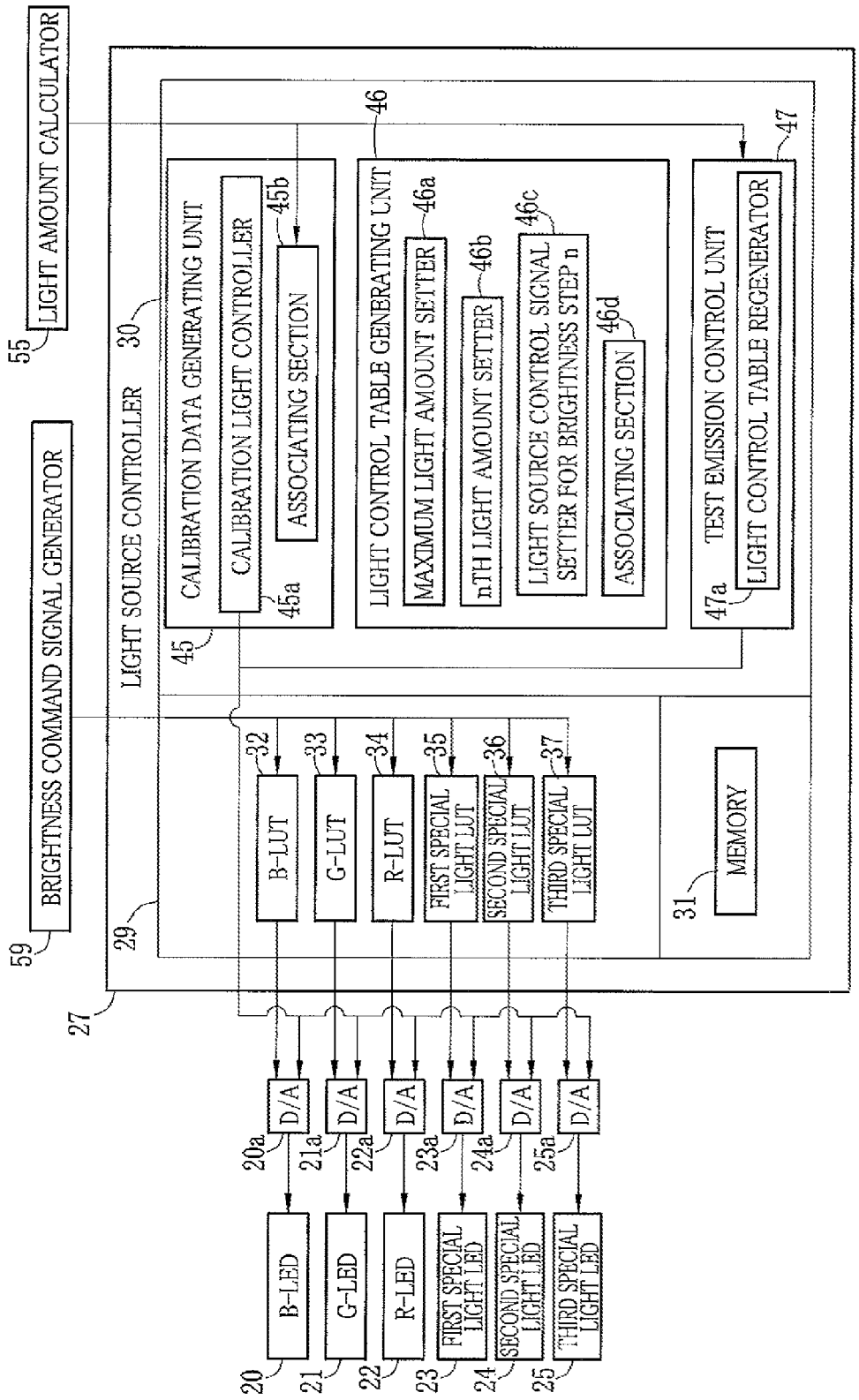

FIG. 11A
SB4 LIGHT CONTROL TABLE
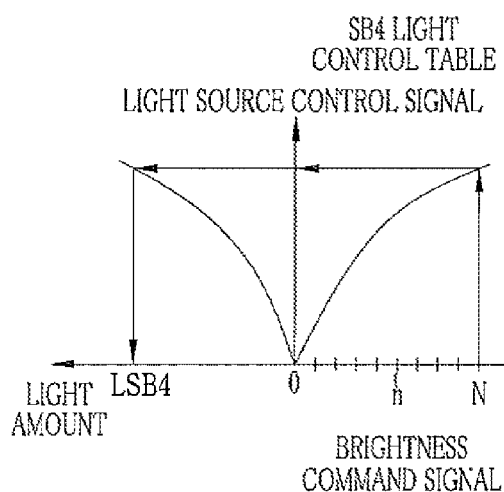
FIG. 11B
SC4 LIGHT CONTROL TABLE
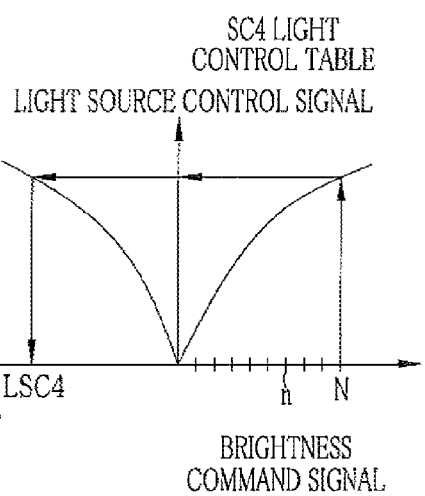
FIG. 12
| CALIBRATION DATA LPB[1] | LIGHT AMOUNT LB1[1] OF BLUE LIGHT B | LIGHT SOURCE CONTROL SIGNAL 1 |
|---|---|---|
| ⋮ | ⋮ | ⋮ |
| CALIBRATION DATA LPB[m] | LIGHT AMOUNT LB1[m] OF BLUE LIGHT B | LIGHT SOURCE CONTROL SIGNAL m |
| ⋮ | ⋮ | ⋮ |
| CALIBRATION DATA LPB[M] | LIGHT AMOUNT LB1[M] OF BLUE LIGHT B | LIGHT SOURCE CONTROL SIGNAL M |

FIG. 13

B1 LIGHT CONTROL TABLE

| BRIGHTNESS COMMAND SIGNAL FOR BRIGHTNESS STEP 1 | LIGHT SOURCE CONTROL SIGNAL 1 |
|---|---|
| ⋮ | ⋮ |
| BRIGHTNESS COMMAND SIGNAL FOR BRIGHTNESS STEP n | LIGHT SOURCE CONTROL SIGNAL n |
| ⋮ | ⋮ |
| BRIGHTNESS COMMAND SIGNAL FOR BRIGHTNESS STEP N | LIGHT SOURCE CONTROL SIGNAL N |

|  | SET SIGNAL RATIO | | |
|---|---|---|---|
|  | R IMAGE SIGNAL | G IMAGE SIGNAL | B IMAGE SIGNAL |
| NORMAL MODE | r1 | g1 | b1 |
| FIRST SPECIAL MODE |  | g2 | b2 |
| SECOND SPECIAL MODE | r3 | g3 | b3 |
| THIRD SPECIAL MODE |  | g4 | b4 |

US 9,107,268 B2

CALIBRATION METHOD AND ENDOSCOPE SYSTEM

CROSS-REFERENCE TO RELATED APPLICATIONS

The present application claims priority under 35 U.S.C. §119 to Japanese Patent Application No. 2013-204301, filed Sep. 30, 2013. The above application is hereby expressly incorporated by reference, in its entirety, into the present application.

BACKGROUND OF THE INVENTION

1. Field of the Invention

The present invention relates to a calibration method and an endoscope system, using semiconductor light sources such as R-, G-, and B-LEDs.

2. Description Related to the Prior Art

Endoscope systems have been widely used in the medical field. The endoscope system comprises a light source device, an endoscope, and a processor device. Endoscopic observation with the endoscope system includes distant-view observation and close-up observation of an observation object. The observation from a distant view is referred to as the distant-view observation. The observation in close proximity to the observation object is referred to as the close-up observation. The observation distance from the observation object is changed depending on the purpose of the observation or diagnosis. A change in the distance from the observation object significantly changes brightness of the observation object. For this reason, it is desirable for the endoscope system to sufficiently ensure a dynamic range (resolution) of illumination light that is used for illuminating the observation object. Since scopes with various levels of sensitivity and color reproducibility are connectable to the endoscope system, ensuring the sufficient dynamic range of the illumination light is also desirable for covering variations between the scopes.

As described in Japanese Pat. No. 4694285, the dynamic range of the illumination light suitable for a scope type is ensured by changing the maximum aperture ratio of an optical diaphragm in accordance with the scope type. However, it is difficult to finely adjust the light amount of the illumination light, namely, to ensure the sufficient dimming resolution, with the use of the optical diaphragm because the optical diaphragm mechanically adjusts the light amount of the illumination light.

Instead of controlling the light amount with the optical diaphragm, a semiconductor light source such as an LED (light emitting diode) may be used as an illumination light source, to widen the dynamic range of the illumination light and to improve the minimum resolution. Thereby, both the light intensity and the emission time of the illumination light are controlled. However, a pulse signal for driving the semiconductor light source is not a perfect rectangular wave, but has a nonlinear shape due to pulse rise delay (overshoot) or pulse fall delay (undershoot). The pulse signal becomes stable in a very short period of time, so that the light which corresponds to the nonlinear portion of the pulse signal due to the pulse rise delay or the like does not cause a problem in a case where the light amount (dose) of the illumination light is high or the emission time of the illumination light is long. However, a ratio of the light which corresponds to the non-linear portion of the pulse signal increases in a case where the dose of the illumination light is extremely small. As a result, the actual dose may differ from the specified dose (target dose). This causes problems, for example, image quality degradation due to a shortage of brightness or color changes.

It is known that wavelengths of light from the LED tend to shift when intensity of the light increases. The wavelength variation (fluctuation) of the LED affects linearity characteristics of the illumination light, resulting in image quality degradation. In a case of narrowband light observation in which narrowband light of specific wavelengths is used, the wavelength variation may change an image of blood vessels and the like. This may also degrades the image quality.

In a case where a semiconductor light source such as the LED is used as the illumination light source as described above, it is desirable to perform high-resolution light amount control in the endoscope system to capture a high-quality image under light of necessary brightness (intensity) and display it while influences of the pulse rise delay, the wavelength variations, and the like are suppressed.

In a case where the illumination light is generated by the combined use of the LEDs of different colors such as an R-LED, a G-LED, and B-LED, instead of the use of the LED of a single color, emission spectra of the light from the respective LEDs are not flat (uniform). Due to the wavelength variations of the LEDs and variations in spectral sensitivities of the image sensors, the combined use of the LEDs of different colors may cause the image quality degradation more frequently than the use of the single color LED. In a case where the LEDs differ from each other in the dimming resolution, the light amounts of the light of the respective colors may vary and cause color changes, depending on the observation mode or the scope type. Such color change problems become more pronounced as the light amount of the illumination becomes extremely small. To reduce the color changes, the color balance may be adjusted by correcting the white balance in accordance with the observation mode or the scope type. However, the white balance correction is not preferred because the white balance correction uses an analog gain that amplifies electric noise. Therefore it is desirable to eliminate the color changes and the like through adjustment of the light intensity ratio among the LEDs while the analog gain is maintained at a low level, to the extent that the noise is not noticeable.

SUMMARY OF THE INVENTION

An object of the present invention is to provide a calibration method and an endoscope system, for high-resolution control of light amounts of semiconductor light sources such as R-, G-, and B-LEDs.

In order to achieve the above and other documents, the calibration method according to the present invention comprises a calibration emission step, a calibration data generating step, a maximum light amount setting step, an nth light amount setting step, a brightness step n light source control signal setting step, and an associating step. In the calibration emission step, a first light source control signal is applied to each semiconductor light source and the each semiconductor light source is allowed to apply each illumination light to a reference object, and a light amount calculator calculates a light amount of the illumination light reflected from the reference object. In the calibration data generating step, calibration data is generated by associating the first light source control signals with the light amounts of the illumination light calculated by the light amount calculator in a case where the first light source control signals are applied. In the maximum light amount setting step, a maximum light amount of the each illumination light is set in accordance with a set light amount ratio and based on the calibration data. In the nth light amount setting step, an nth light amount for the each illumination light is set based on the maximum light amount for the each illumination light. The nth light amount increases or decreases linearly relative to the brightness step n. In the brightness step n light source control signal setting step, the calibration data is referred to, and a light source control signal corresponding to the nth light amount, of the first light source control signals, is determined. The determined light source control signal is set as a second light source control signal corresponding to the brightness step n. In the associating step, the second light source control signal is associated with a brightness control signal n for the brightness step n, and thereby a light control table is generated. The calibration method for an endoscope system has semiconductor light sources for emitting different types of illumination light with different wavelength ranges, a light source controller for controlling the semiconductor light sources with respective light source control signals, and a brightness command signal generator for generating a brightness command signal n for commanding the light source controller to change a light amount of the each illumination light based on a brightness step n (n is an integer from 0 to N−1) of N (N is an integer greater than or equal to 2) levels. A light amount ratio between light amounts of the illumination light are set as the set light amount ratio in advance.

It is preferred that a ratio of a light amount of specific illumination light is set to be the highest of ratios of the light amounts of the different types of the illumination light. In the maximum light amount setting step, a highest light amount of the specific illumination light in the calibration data is set as the maximum light amount of the specific illumination light. A maximum light amount of the illumination light other than the specific illumination light is set based on the maximum light amount of the specific illumination light and the set light amount ratio. It is preferred that the maximum light amount of the illumination light other than the specific illumination light is calculated by multiplying the maximum light amount of the specific illumination light by a control signal ratio for controlling the light amount relative to the light amount of the specific illumination light. The control signal ratio is obtained based on the set light amount ratio. It is preferred that, in the nth light amount setting step, the nth light amount of the each illumination light, corresponding to the brightness step n, is obtained based on a value calculated by dividing the maximum light amount of the each illumination light by N.

It is preferred that the calibration method further comprises a test emission step, a first error calculation step, and a light control table regeneration step. In the test emission step, emission of the each semiconductor light source is controlled based on the light control table and the reference object is illuminated with the each illumination light, and a light amount of the each illumination light reflected from the reference object is calculated with a light amount calculator. In the first error calculation step, an error between the each light amount corresponding to the brightness step n, calculated in the test emission step, and a target light amount of the each illumination light is calculated. In the light control table generating step, whether the error is within a predetermined range or not is determined. The light control table is not regenerated in a case where the error is within the predetermined range. The light control table is regenerated in a case where the error is out of the predetermined range.

It is preferred that the light control table regeneration step has a resetting step, a second error calculation step, a selecting step, and a re-associating step. In the resetting step, a light amount of the each illumination light is reset in accordance with the set light amount ratio and based on the light amount of the illumination light with the largest error, in the case where the error is out of the predetermined range. In the second error calculation step, an error is calculated between a light amount of the each illumination light after resetting and the target light amount of the each illumination light. In the selecting step, the light amount of the illumination light with the smaller of the errors calculated in the first or second error calculation step is selected. In the re-associating step, the calibration data is referred to, and a third light source control signal, which corresponds to the light amount of the illumination light selected in the selecting step, is determined from the first light source control signals. The determined third light source control signal is re-associated with the brightness command signal n that corresponds to the brightness step n in the light control table.

It is preferred that the calibration method further comprises a joint table generating step in which a joint table is generated by joining a control signal correction table, in which the second light source control signal is associated with a linear-change light source control signal for linearly increasing or decreasing the light amount of the each illumination light, and the light control table.

It is preferred that the semiconductor light sources have an R-LED for emitting red light, a G-LED for emitting green light, and a B-LED for emitting blue light. It is preferred that the semiconductor light sources have special light LEDs. The special LEDs at least includes a first special light LED and a second special light LED. The first special light LED emits first special light having a first wavelength range. The second special light LED emits second special light having a second wavelength range. The first and second wavelength ranges differ from wavelength ranges of the red light, the green light, and the blue light.

It is preferred that the endoscope system has a normal mode, in which at least the R-LED, the G-LED, and the B-LED are turned on to emit white light, and a special mode, in which at least the first and second special light LEDs are turned on to emit special light. It is preferred that at least the maximum light amount setting step, the nth light amount setting step, the brightness step n light source control signal setting step, and the light control table generating step are performed in the each observation mode to generate the light control tables which differ between the normal and the special modes.

The emission of each semiconductor light source is controlled based on the light control table generated by the calibration method according to the present invention. It is preferred that the endoscope system comprises a storage unit, in which a scope ID of an endoscope is associated with the light control table and stored, and an ID reader for reading out the scope ID of the endoscope.

The endoscope system comprises a calibration light controller, a light amount calculator, a first associating section, a maximum light amount setter, an nth light amount setter, a light source control signal setter, and a second associating section. The calibration light controller applies a first light source control signal to the each semiconductor light source, and allows the each semiconductor light source to emit the each illumination light to a reference object. The light amount calculator calculates a light amount of the each illumination light reflected from the reference object. The first associating section generates calibration data by associating the first light source control signals with the light amounts of the illumination light calculated by the light amount calculator in a case where the first light source control signals are applied. The maximum light amount setter sets a maximum light amount of the each illumination light in accordance with the set light amount ratio and based on the calibration data. The nth light amount setter sets an nth light amount for the each illumination light based on the maximum light amount of the each illumination light. The nth light amount increases or decreases linearly relative to the brightness step n. The light source control signal setter refers to the calibration data and determines a light source control signal corresponding to the nth light amount from the first light source control signals, and sets the determined light source control signal as a second light source control signal corresponding to the brightness step n. The second associating section associates the second light source control signal with the brightness command signal n for the brightness step n, and thereby generates a light control table. The endoscope system has semiconductor light sources for emitting different types of illumination light with different wavelength ranges, a light source controller for controlling the semiconductor light sources with respective light source control signals, and a brightness command signal generator for generating a brightness command signal n for commanding the light source controller to change a light amount of the each illumination light based on a brightness step n (n is an integer from 0 to N−1) of N (N is an integer greater than or equal to 2) levels. The light amount ratio between the different types of the illumination light is set as a set light amount ratio in advance.

The calibration method according to the present invention comprises a calibration emission and imaging step, a specific light source control signal setting step, a reference light source control signal setting step, a control signal ratio calculating step, a brightness step n light source control signal setting step, and an associating step. In the calibration emission and imaging step, a light source control signal is applied to the each semiconductor light source and the each semiconductor light source is allowed to emit the each illumination light to a reference object, and the reference object is imaged with the color image sensor. In the specific light source control signal setting step, the each light source control signal which makes a signal ratio between image signals of different colors obtained by imaging the reference object and outputted from the color image sensor equivalent to the set signal ratio is set as a specific light source control signal. In the reference light source control signal setting step, the light source control signal which is applied to the semiconductor light source with high light emission is set as a reference light source control signal. The highest of the specific light source control signals is applied to the semiconductor light source with the high light emission. In the control signal ratio calculating step, a control signal ratio between the specific light source control signals is obtained. In the light source control signal setting step, the light source control signal for the brightness step n is obtained for the each semiconductor light source based on the reference light source control signal and the control signal ratio. The light source control signal for the brightness step n corresponds to the brightness step n. In the associating step, the light source control signal for the brightness step n and the brightness command signal n for the brightness step n are stored in the light control table such that the light source control signal for the brightness step n is associated with the brightness command signal n for the brightness step n. The endoscope system has semiconductor light sources for emitting different types of illumination light with different wavelength ranges, a light source controller for controlling the semiconductor light sources with respective light source control signals, a brightness command signal generator for generating a brightness command signal n for commanding the light source controller to change a light amount of the each illumination light based on a brightness step n (n is an integer from 0 to N−1) of N (N is an integer greater than or equal to 2) levels, and a color image sensor. A signal ratio between image signals of different colors is set in advance as a set signal ratio. The image signals are obtained by imaging an observation object under the different types of the illumination light with the color image sensor.

It is preferred that, in the brightness step n light source control signal setting step, the light source control signal for the brightness step n, for the semiconductor light source with the high light emission, is calculated by dividing the reference light source control signal by N. The light source control signal for the brightness step n, for the semiconductor light source other than the high-emission semiconductor light source, is calculated by multiplying the reference light source control signal by the control signal ratio.

According to the present invention, the light control table which allows the high-resolution control of the light amounts of the semiconductor light sources are produced. By controlling the emission of each semiconductor light source based on the light control table, the light amount of each illumination light is adjusted while the set light amount ratio is maintained, regardless of the value of the brightness command signal n. Thus, the color changes and the like are prevented. Consequently, the dimming resolution and the dynamic range of the illumination light corresponding to the set light amount ratio are ensured sufficiently. Since the light control table is generated based on the calibration data, which is obtained by using the light source device and the endoscope actually used for imaging the reference object, the light control table is adjusted to make the signals, which are obtained by imaging the reference object, constant even if there are differences in emission spectrum properties between the semiconductor light sources of the light source devices and differences in spectral sensitivity properties between the endoscopes. By using the light control table of the present invention, the light amount is controlled with high resolution and without influence of the variations even if the emission spectrum properties may vary among the semiconductor light sources and the spectral sensitivities may vary among the endoscopes.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein:

FIG. 4 is a table illustrating an emission state of each LED in each observation mode;

FIG. 5 is a table illustrating a set light amount ratio of each observation mode;

FIG. 6A is a block diagram illustrating functions of a light source controller;

FIGS. 11A and 11B are graphs illustrating, on their right sides, relationships between the brightness control signals and the light source control signals in SB4 and SC4 light control tables, respectively, and, on their left sides, relationships between the light source control signals and light amounts LSB4 and LSC4 of the second special light SB and the third special light SC emitted based on the light source control signals, respectively;

FIG. 12 is a table illustrating calibration data in which light amounts of the blue light B are associated with the respective light source control signals;

FIG. 13 illustrates the B1 light control table in which brightness command signals for brightness steps n are associated with the respective light source control signals;

DESCRIPTION OF THE PREFERRED EMBODIMENTS

First Embodiment

Figure 1:
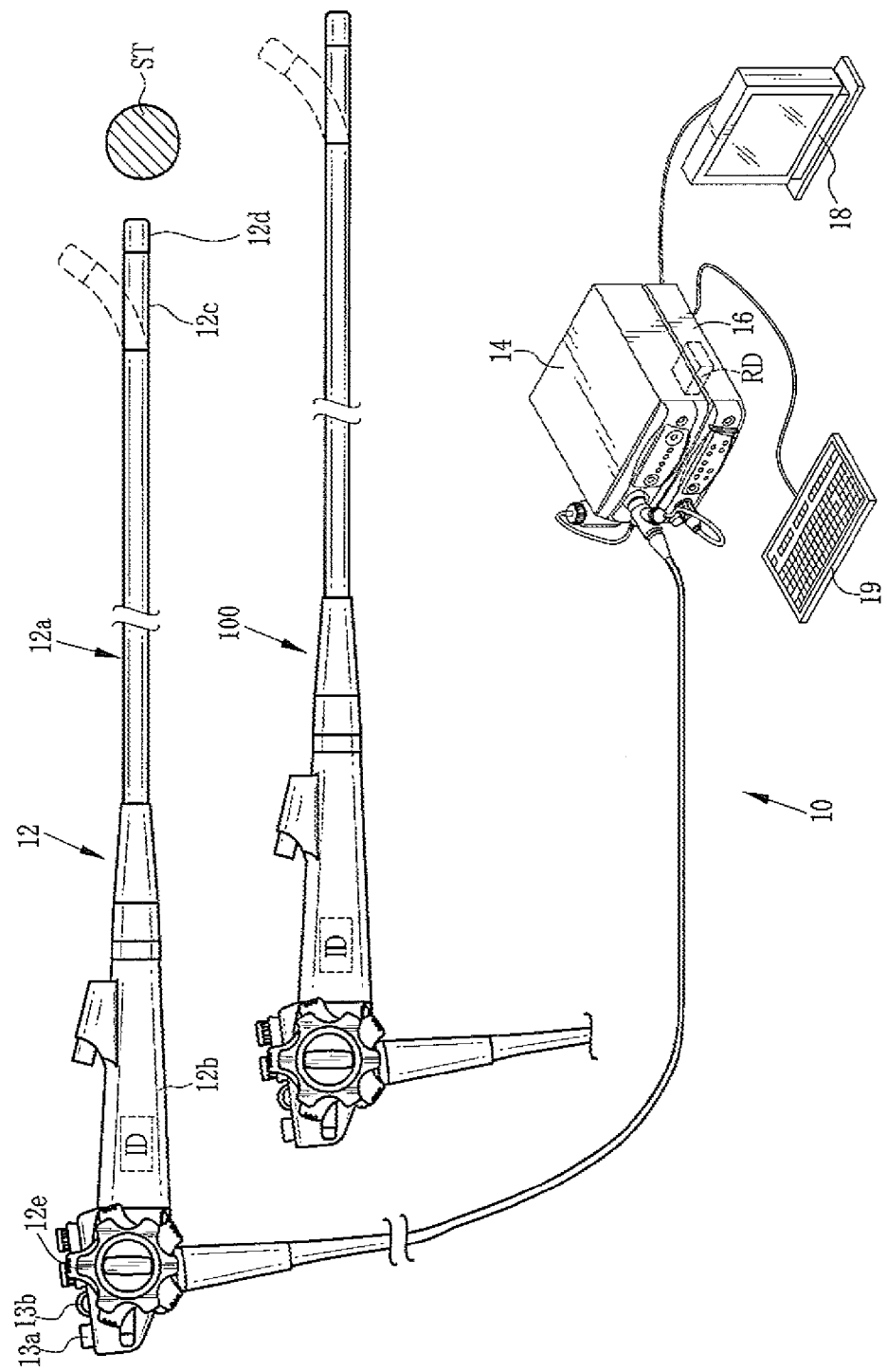
FIG. 1 is an external view of an endoscope system.

As shown in FIG. 1, an endoscope system 10 of a first embodiment comprises an endoscope 12, a light source device 14, a processor device 16, a monitor 18, and a console 19. The endoscope 12 is connected optically to the light source device 14, and electrically to the processor device 16. The endoscope 12 comprises an insertion section 12a to be inserted into a body cavity, a control handle unit 12b provided at the proximal end of the insertion section 12a, a flexible portion 12c, and a distal portion 12d. The distal portion 12d is coupled to the flexible portion 12c, which is coupled to the distal side of the insertion section 12a. The flexible portion 12c is bent by operating an angle knob 12e of the control handle unit 12b. The distal portion 12d is directed to a desired direction by bending the flexible portion 12c.

The control handle unit 12b is provided with the angle knob 12e, a mode switch (SW) 13a, and a zoom operating section 13b. The mode SW 13a is operated to switch among a normal mode, special modes, and a calibration mode. In the normal mode, a normal image of an observation object is captured under normal light such as white light and displayed on the monitor 18. In the special mode, a special image of the observation object is captured under special light of predetermined wavelengths and displayed on the monitor 18. In the calibration mode, the light source control, signal processing, or the like is calibrated after the endoscope 12 is connected to the light source device 14 or the processor device 16. The special modes include a first special mode, a second special mode, and a third special mode. The zoom operating section 13b is used for driving a zooming lens 51b (see FIG. 2). The zooming lens 51b is moved to a telephoto side to magnify the observation object.

The processor device 16 is electrically connected to the monitor 18 and the console 19. The monitor 18 outputs and displays image information and the like. The console 19 functions as a UI (user interface), which receives input operation such as setting a function. Note that an external storage unit (not shown) for recording the image information and the like may be connected to the processor device 16.

An endoscope 100, which differs from the endoscope 12, may be connected to the light source device 14 and the processor device 16. The endoscope 100 has an image sensor which differs in spectral sensitivity from an image sensor 51c (see FIG. 2) of the endoscope 12. Other than that, the endoscope 100 is substantially the same as the endoscope 12.

Figure 2:
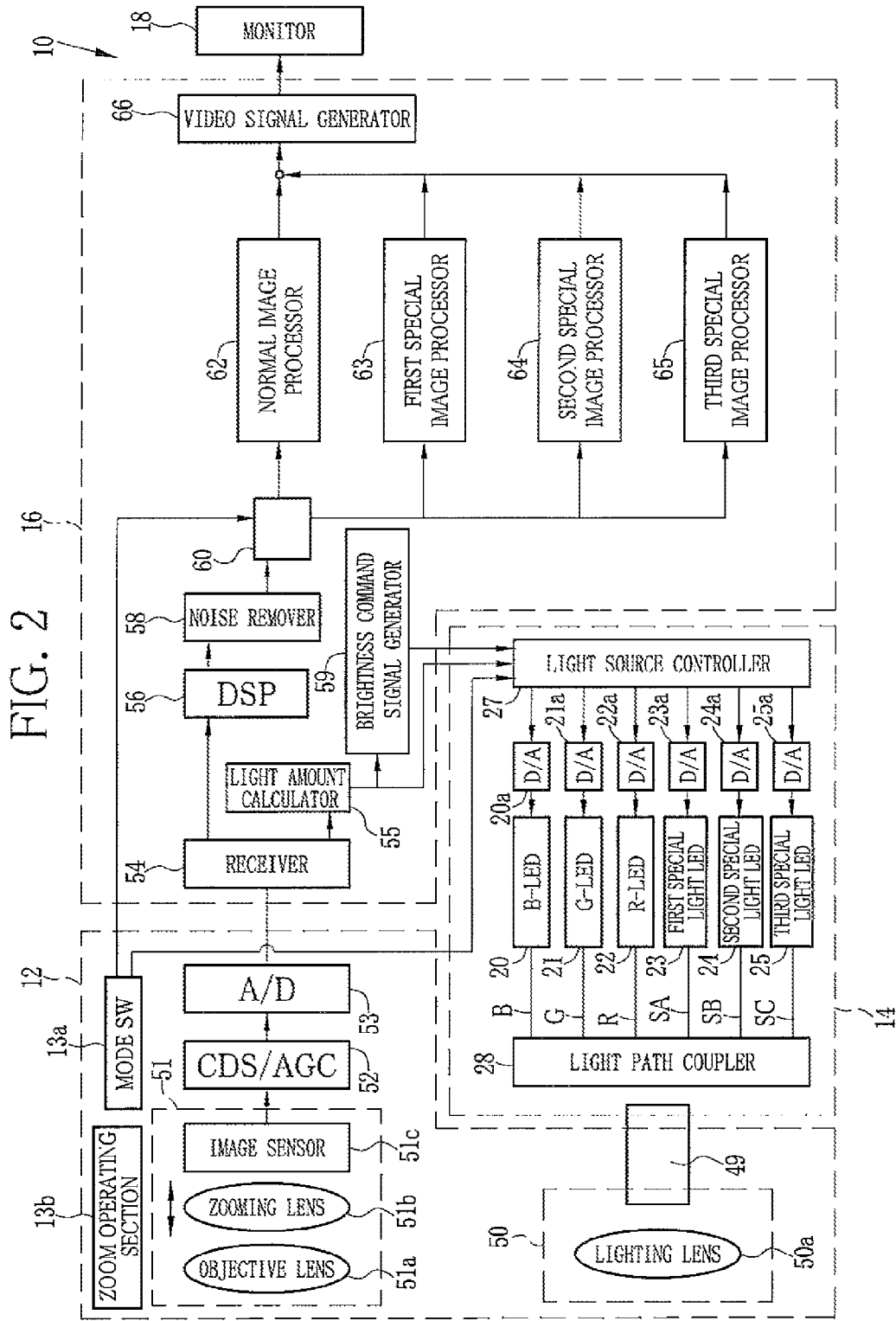
FIG. 2 is a block diagram illustrating functions of the endoscope system.

As shown in FIG. 2, the light source device 14 comprises a B-LED (Blue Light Emitting Diode) 20, a G-LED (Green Light Emitting Diode) 21, an R-LED (Red Light Emitting Diode) 22, a first special light LED 23, a second special light LED 24, a third special light LED 25, a light source controller 27 for controlling the six LEDs 20 to 25, an optical path coupler 28 for coupling the optical paths of the light from the six LEDs 20 to 25. The light combined through the optical path coupler 28 are applied to the observation object through a light guide 49 and a lighting lens 50a. The light guide 49 extends inside the insertion section 12a. Note that an LD (Laser Diode) may be used instead of the LED.

The light guide 49 extends through a universal cord that connects the endoscope 12 and the light source device 14, and transmits the light integrated by the optical path coupler 28 to the distal portion 12d of the endoscope 12. Note that a multimode fiber is used as the light guide 49. For example, a small-diameter fiber cable with the core diameter 105 μm, the clad diameter 125 μm, and the outer diameter φ 0.3 to 0.5 mm (including a protection layer, being a jacket) may be used.

The B-LED 20 generates blue light B having a specific wavelength range in a blue region. The G-LED 21 generates green light G having a specific wavelength range in a green region. The R-LED 22 generates red light R having a specific wavelength range in a red region. The first special light LED 23 generates first special light SA that is used in the first and second special modes. The first special light SA has a first wavelength range. The second special light LED 24 generates second special light SB that is used in the first, second and third special modes. The second special light SB has a second wavelength range, which differs from the first wavelength range. The third special light LED 25 generates third special light SC that is used in the third special mode. The third special light SC has a third wavelength range, which differs from the first and second wavelength ranges.

Figure 3:
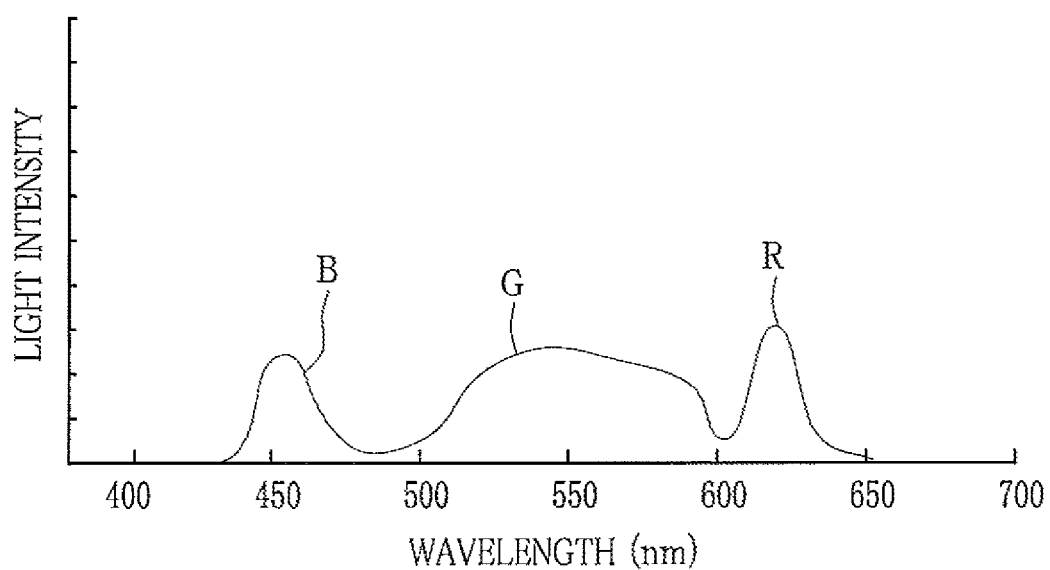
FIG. 3 is a graph illustrating emission spectra of blue light B, green light G, and red light R.

Of the above-described six types of light, note that the blue light B preferably has the wavelength range on a somewhat short-wavelength side with the center wavelength of 395 to 410 nm as shown in FIG. 3. The green light G is preferably normally-distributed light with a wavelength range of 430 to 600 nm. The red light R preferably has a wavelength range of 600 to 650 nm with the center wavelength of 620 to 630 nm.

Digital/analog converters (D/As) 20a to 25a are provided upstream from the respective LEDs 20 to 25 and downstream from the light source controller 27. Each of the D/As 20a to 25a converts a digital light source control signal from the light source controller 27 into an analog light source control signal. Based on the analog light source control signals, emission conditions of the LEDs 20 to 25 are controlled, respectively. Note that the emission conditions include light intensity and emission time of each of the LEDs 20 to 25.

The light source controller 27 transmits the light source control signals to the respective LEDs 20 to 25 to control the emissions of the LEDs 20 to 25. The light source controller 27 receives a brightness command signal from a brightness command signal generator 59 of the processor device and controls the emission of each of the LEDs 20 to 25 such that the light amount of each of the LEDs 20 to 25 is changed to a brightness step n (nth level) of N levels. Here, a light source control signal "m" is composed of a digital signal of M bits. A brightness command signal "n" is composed of a digital signal of N bits. Note that "M" is an integer greater than or equal to 2, and greater than or equal to N, and "m" is an integer which is one of 1 to M. "N" is an integer greater than or equal to 2, and "n" is an integer which is one of 0 to N−1. "M" is greater than "N" (M>N). Of the M light source control signals m, the N light source control signals are used for the control of the light sources with the use of the light control tables below.

As shown in FIGS. 4 and 5, the light source controller 27 controls the LEDs 20 to 25 based on the emission conditions, which differ among the observation modes. In the normal mode, the light source controller 27 turns on the B-LED 20, the G-LED 21, the R-LED 22, the first special light LED 23, and the second special light LED 24, and sets a light amount ratio LB1:LG1:LR1:LSA1:LSA2, among the light amounts of the blue light B, the green light G, the red light R, the first special light SA, and the second special light SB from the respective five LEDs 20 to 24, to a set light amount ratio X1, in which the ratio of the light amount of the LB1 is the highest of all, and LSA1=LB1×w1% and LSA2=LB1×w2% where w1 and w2 are numbers between 0 to 100.

In the first special mode, the light source controller 27 turns on the G-LED 21, the first special light LED 23, and the second special light LED 24, and sets a light amount ratio LG2:LSA2:LSB2, among the light amounts of the green light G, the first special light SA, and the second special light SB from the respective LEDs 21, 23, and 24, to a set light amount ratio X2, in which the ratio of the light amount of the LSA2 is the highest of all, and LSB2=LSA2×t1% where t1 is a number between 0 to 100. In the second special mode, the light source controller 27 turns on the G-LED 21, the R-LED 22, the first special light LED 23, and the second special light LED 24, and sets a light amount ratio LG3:LR3:LSA3:LSB3, among the green light G, the red light R, the first special light SA, and the second special light SB from the respective four LEDs 21 to 24, to a set light amount ratio X3 in which the ratio of the light amount of the LSA3 is the highest of all and LSB3=SA3×t2% where t2 is a number between 0 to 100. In the third special mode, the light source controller 27 turns on the second special light LED 24 and the third special light LED 25, and sets a light amount ratio LSB4:LSC4, between the second special light SB and the third special light SC from the respective LEDs 24 and 25, to a set light amount ratio X4 in which LSC4>LSB4.

Figure 6B:
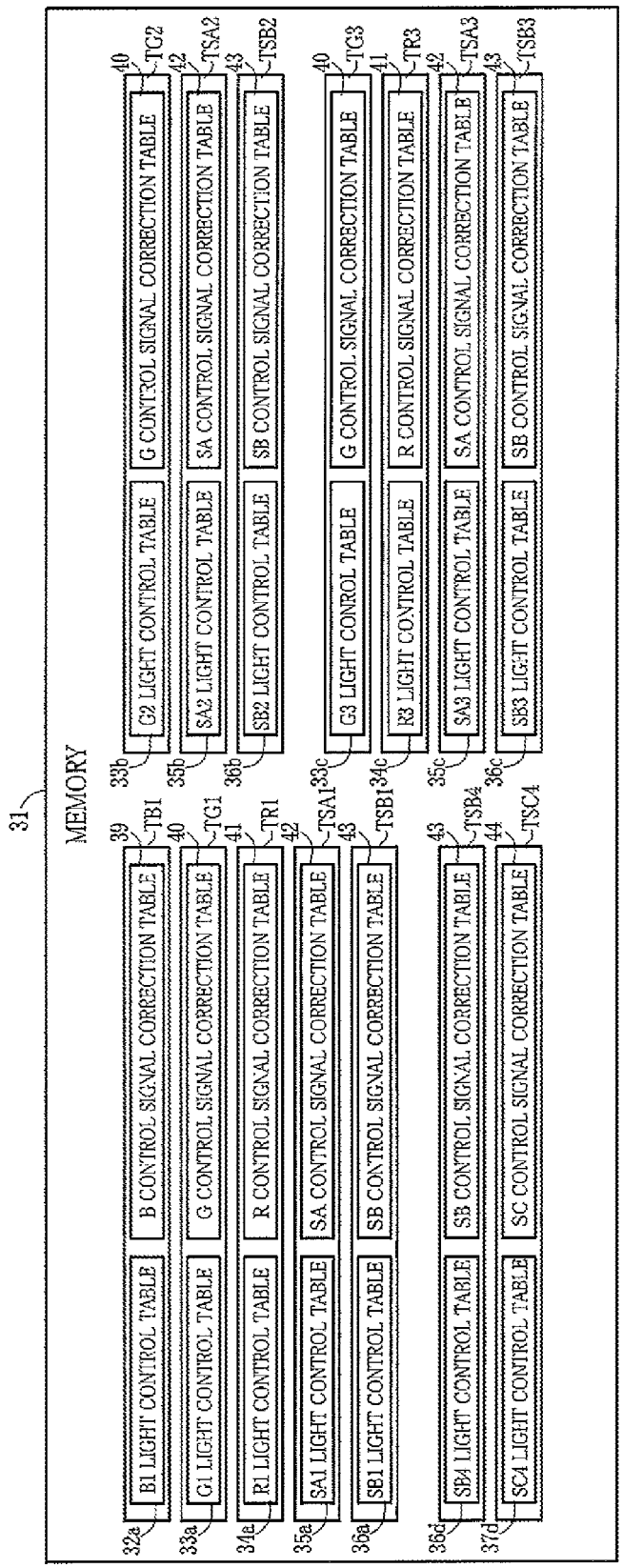
FIG. 6B is a bock diagram illustrating contents stored in a memory inside the light source controller.
Figure 7A:
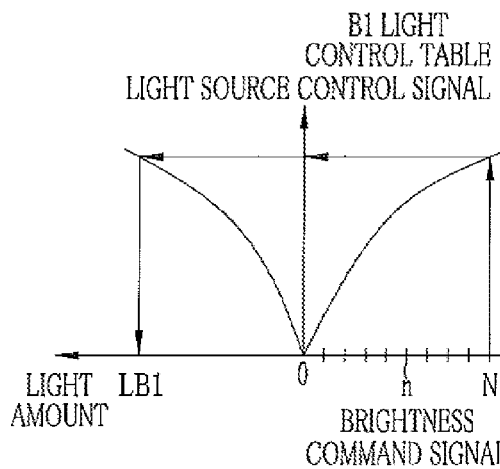
FIGS. 7A to 7E are graphs illustrating, on their right sides, relationships between brightness command signals and light source control signals in B1, G1, R1, SA1, and SB1 light control tables, respectively, and, on their left sides, relationships between the light source control signals and light amounts LB1, LG1, LR1, LSA1, and LSB1 of blue light B, green light G, red light R, first special light SA, and second special light SB emitted based on the light source control signals, respectively.
Figure 7B:
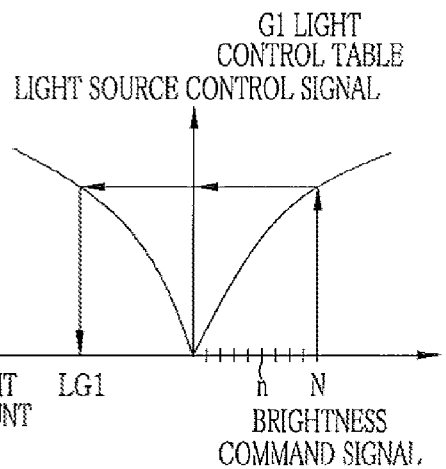
Figure 7C:
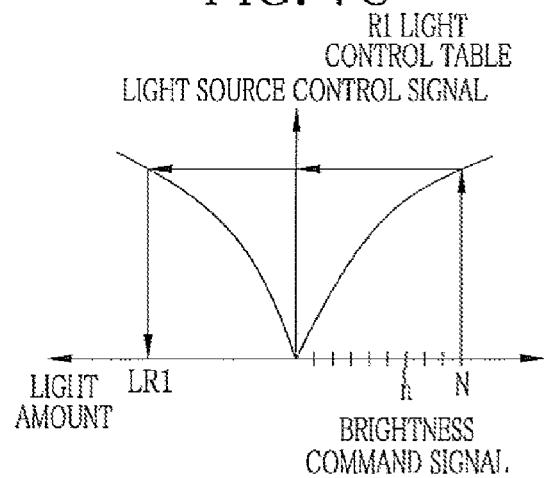
Figure 7D:
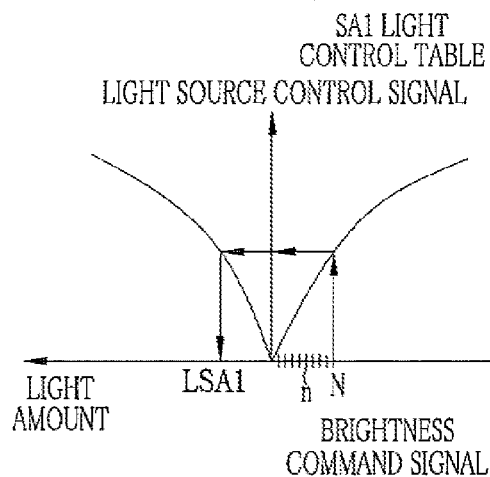
Figure 7E:
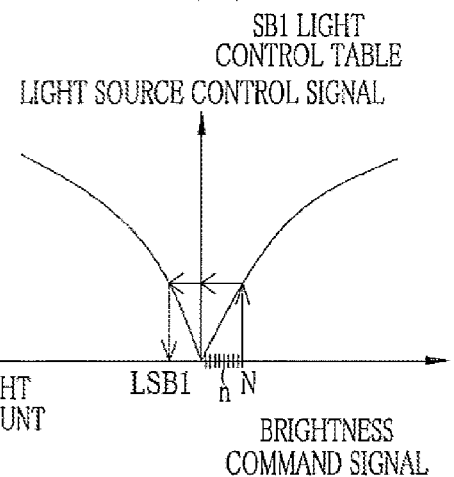

As shown in FIG. 6A, the light source controller 27 comprises an observation circuit 29, which is used in the normal mode and the special modes, a calibration circuit 30, which is used in the calibration mode, and a memory 31. The observation circuit 29 comprises a B-LUT (Look Up Table) 32 connected to the B-LED 20, a G-LUT 33 connected to the G-LED 21, an R-LUT 34 connected to the R-LED 22, a first special light LUT 35 connected to the first special light LED 23, a second special light LUT 36 connected to the second special light LED 24, and a third special light LUT 37 connected to the third special light LED 25.

Each of the LUTs 32 to 37 has a joint table, in which two types of tables, a light control table and a control signal correction table, are joined together. Each light control table is used for controlling each of the LEDs 20 to 25. Each control signal correction table is used for correcting wavelength variations (shifting of a peak wavelength of the LED to a long or short wavelength side) of each of the LEDs 20 to 25. In each observation mode, the joint tables are sequentially read-out from the memory 31 (see FIG. 6B).

In the normal mode, the joint tables TB1, TG1, TR1, TSA1, and TSB1 are read out. In the joint tables TB1, TG1, TR1, TSA1, and TSB1, a B1 light control table 32a, a G1 light control table 33a, an R1 light control table 34a, an SA1 light control table 35a, and an SB1 light control table 36a, which are for the normal mode, are joined to a B control signal correction table 39, a G control signal correction table 40, an R control signal correction table 41, an SA control signal correction table 42, and an SB control signal correction table 43, respectively. The joint tables TB1, TG1, TR1, TSA1, and TSB1 are stored in the B-LUT 32, the G-LUT 33, the R-LUT 34, the first special light LUT 35, and the second special light LUT 36, respectively.

Graphs on the right sides of FIGS. 7A to 7E illustrate the relationships, between the brightness command signals n and the light source control signals m, which are stored in the B1 light control table, the G1 light control table, the R1 light control table, the SA1 light control table, and the SB1 light control table 32a to 36a, respectively. Based on the light control tables 32a to 36a, five light source control signals which correspond to the LEDs 20 to 24 are determined, respectively, relative to the single brightness command signal n. As shown by graphs on the left sides of FIGS. 7A to 7E, the LEDs 20 to 24 emit the light with the light amounts LB1, LG1, LR1, LSA1, and LSB1, based on the five light source control signals, respectively. The light amount ratio among the light amounts of the light of these five colors substantially coincides with the predetermined set light amount ratio X1, and maintains itself substantially at the set light amount ratio X1 regardless of the value of the brightness command signal n.

Figure 8:
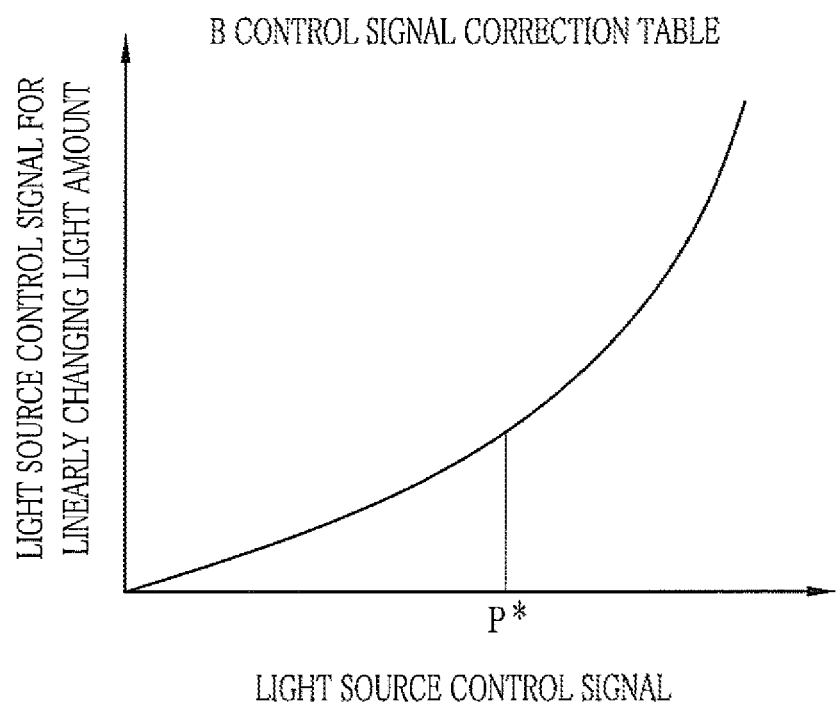
FIG. 8 is a graph illustrating a relationship between the light source control signal and a light source control signal for linearly changing the light amount.

The B, G, R, SA, and SB control signal correction tables 39, 40, 41, 42, and 43 store the light source control signals and the light source control signals (hereinafter referred to as the corrected light source control signals) for linearly increasing or decreasing the light amounts of the LEDs 20 to 24, in a way that the light source control signals and the corrected light source control signals (linear-change light source control signals) are associated with each other. As shown in FIG. 8, in the B control signal correction table 39, the relationship between the light source control signal and the corrected light source control signal differs between a case where the light source control signal is less than or equal to a given value P* and a case where the light source control signal is greater than the given value P*.

The reason for setting the relationship between the light source control signal and the corrected light source control signal (light source control signal for linearly increasing or decreasing the light amount) as shown in FIG. 8 is as follows. In a case where the light source control signal is less than or equal to the given value P*, namely, the intensities of the light from the LEDs 20 to 24 are low, the wavelength variations do not occur in the LEDs 20 to 24, so that the light amounts of the respective LEDs 20 to 24 increase or decrease linearly. In a case where the light source control signal exceeds the given value P*, namely, the intensities of the light from the LEDs 20 to 24 are high, the wavelength variations occur in the LEDs 20 to 24. In this case, the light amounts of the respective LEDs 20 to 24 do not increase or decrease linearly. In this example, the relationship between the light source control signal and the corrected light source control signal differs between the case where the light source control signal exceeds the given value P* and the case where the light source control signal is less than or equal to the given value P*, so that the light amounts of the respective LEDs 20 to 24 increase or decrease linearly. Note that the control signal correction tables 40 to 43 also satisfy the relationship illustrated in FIG. 8, in a manner similar to the control signal correction table 39.

In the normal mode, the light control tables 32a to 36a are referred to when the brightness command signal n is inputted to each of the LUTs 32 to 36. Thereby, the light source control signals n which correspond to the inputted brightness command signal n are selected. Then, the control signal correction tables 39 to 43 are referred to, and the corrected light source control signals which correspond to the selected light source control signals n are selected, respectively. Based on the corrected light source control signals (the light source control signals n for linearly changing the light mounts), the LEDs 20 to 24 emit the blue light B, the green light G, the red light R, the first special light SA, and the second special light SB, respectively.

The light amount ratio among the light of these five colors maintains itself at the set light amount ratio X1. Since the light source control signals are set to linearly change the light amounts of the LEDs 20 to 24, the light amount ratio among the light of the five colors maintains itself at the set light amount ratio X1 without a shift even if one of the light intensities of the LEDs 20 to 24 increases and causes the wavelength variations. Note that the LUTs 32 to 36 store the joint tables TB1, TG1, TR1, TSA1, and TSB1, respectively. In the joint tables TB1, TG1, TR1, TSA1, and TSB1, the light control tables 32a to 36a are joined to the control signal correction tables 39 to 43, respectively. Thereby, the corrected light source control signal (the light source control signal n for linearly changing the light amount) is outputted directly in response to the input of the brightness command signal n.

In the first special mode, the joint tables TG2, TSA2, and TSB2 are read out from the memory 31. In the joint tables TG2, TSA2, and TSB2, the G2 light control table 33b, the SA2 light control table 35b, and the SB2 light control table 36b, which are for the first special mode, are joined to the G control signal correction table 40, the SA control signal correction table 42, and the SB control signal correction table 43, respectively. The joint tables TG2, TSA2, and TSB2 are stored in the G-LUT 33, the first special light LUT 35, and the second special light LUT 36, respectively.

Figure 9A:
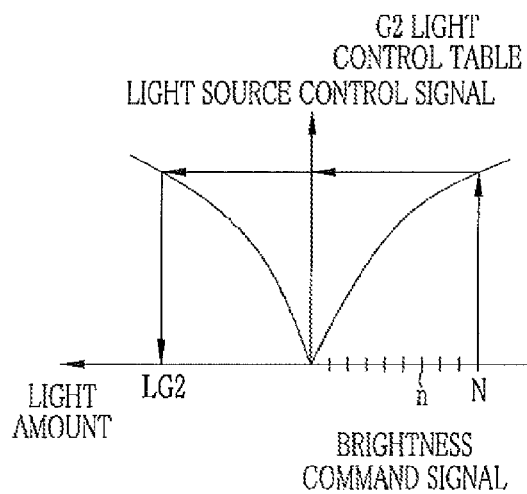
FIGS. 9A to 9C are graphs illustrating, on their right sides, relationships between the brightness command signals and the light source control signals in G2, SA2, and SB2 light control tables, respectively, and, on their left sides, relationships between the light source control signals and light amounts LG2, LSA2, and LSB2 of the green light G, the first special light SA, and the second special light SB emitted based on the light source control signals, respectively.
Figure 9B:
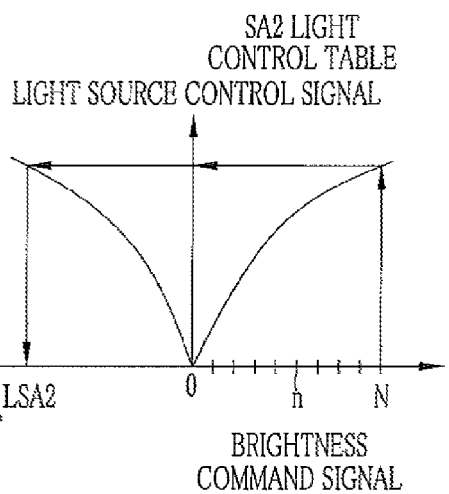
Figure 9C:
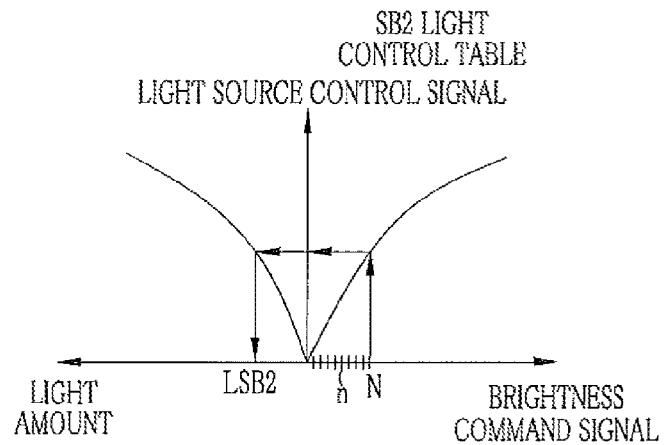
Figure 10A:
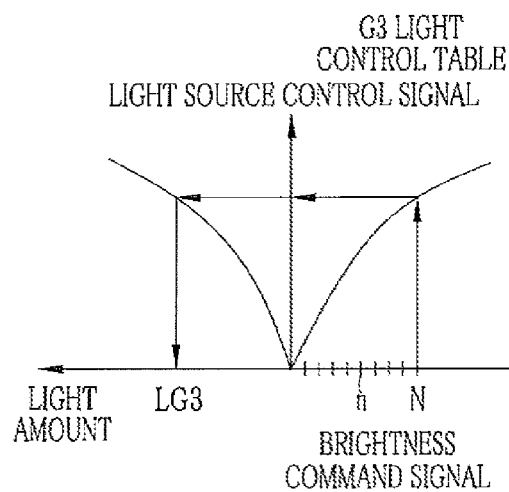
FIGS. 10A to 10D are graphs illustrating, on their right sides, relationships between the brightness control signals and the light source control signals in G3, R3, SA3, and SB3 light control tables, respectively, and, on their left sides, relationships between the light source control signals and light amounts LG3, LSA3, and LSB3, of the green light G, the red light R, the first special light SA, and the second special light SB emitted based on the light source control signals, respectively.
Figure 10B:
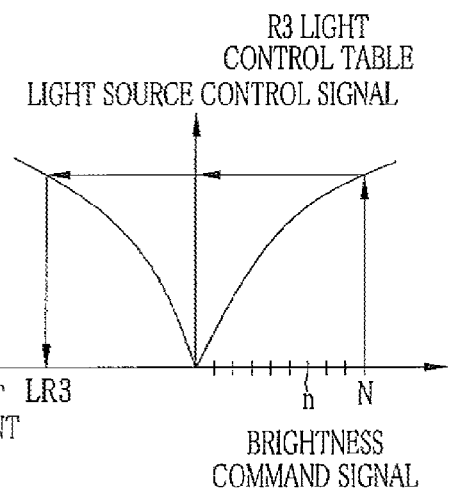
Figure 10C:
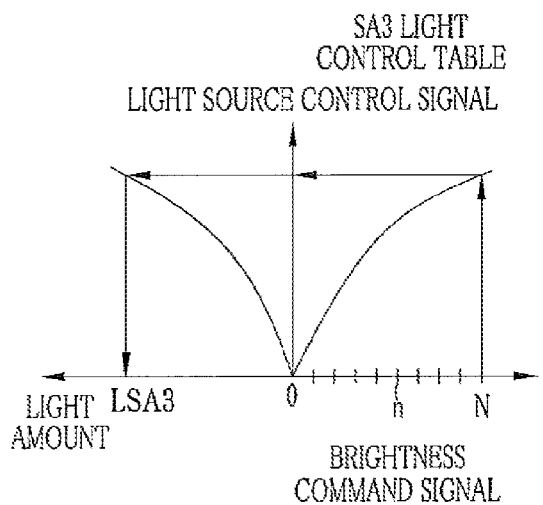
Figure 10D:
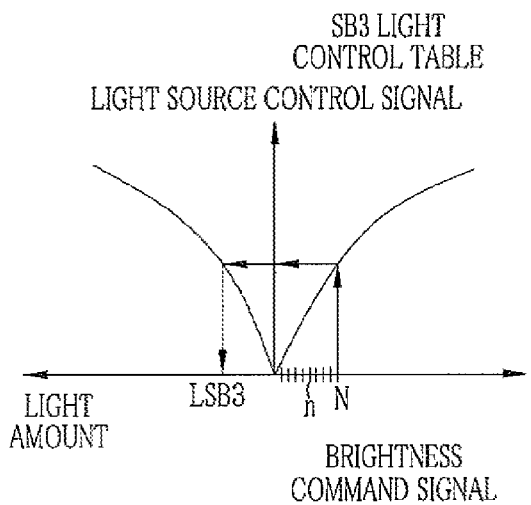

Graphs on the right sides of FIG. 9A to 9C illustrate relationships, between the brightness command signals and the light source control signals, which are stored in the light control tables 33b, 35b, and 36b for the first special mode, respectively. Based on the light control tables 33b, 35b, and 36b, the three light source control signals n which correspond to the LEDs 21, 23, and 24 are determined, respectively, relative to the single brightness command signal n. As shown by graphs on the left sides of FIGS. 9A to 9C, the LEDs 21, 23, and 24 emit the light with the light amounts LG2, LSA2, and LSB2, based on the three light source control signals n, respectively. The light amount ratio among the light amounts of these three colors substantially coincides with the predetermined set light amount ratio X2, and maintains itself substantially at the set light amount ratio X2 regardless of the value of the brightness command signal n. The control signal correction tables 40, 42, and 43 are the same as those stored in the LUTs 33, 35, and 36 in the normal mode.

In the second special mode, the joint tables TG3, TR3, TSA3, and TSB3 are read out from the memory 31. In the joint tables TG3, TR3, TSA3, and TSB3, the G3 light control table 33c, the R3 light control table 34c, the SA3 light control table 35c, and the SB3 light control table 36c, which are used in the second special mode, are joined to the G control signal correction table 40, the R control signal correction table 41, the SA control signal correction table 42, and the SB control signal correction table 43, respectively. The joint tables TG3, TR3, TSA3, and TSB3 are stored in the G-LUT 33, the R-LUT 34, the first special light LUT 35, and the second special light LUT 36, respectively.

The graphs on the right sides of FIGS. 10A to 10D illustrate the relationships, between the brightness command signals and the light source control signals, stored in the light control tables 33c, 34c, 35c, and 36c for the second special mode, respectively. Based on the light control tables 33c, 34c, 35c, and 36c, the four light source control signals n which correspond to the LEDs 21, 22, 23, and 24 are determined, respectively, relative to the single brightness command signal n. As shown by graphs on the left sides of FIGS. 10A to 10D, the LEDs 21, 22, 23, and 24 emit the light with the light amounts LG3, LR3, LSA3, and LSB3, in response to the four light source control signals n, respectively. The light amount ratio among the light of these four colors substantially coincides with the predetermined set light amount ratio X3. The light amount ratio among the light of the four colors maintains itself substantially at the set light amount ratio X3 regardless of the value of the brightness command signal n. The control signal correction tables 40, 41, 42, and 43 are the same as those stored in the LUTs 33, 34, 35, and 36 in the normal mode.

In the third special mode, joint tables TSB4 and TSC4 are read out from the memory 31. In the joint tables TSB4 and TSC4, the SB4 light control table 36d and the SC4 light control table 37d, which are used in the third special mode, are joined to the SB control signal correction table 43 and the SC control signal correction table 44, respectively. The joint tables TSB4 and TSC4 are stored in the second special light LUT 36 and the third special light LUT 37, respectively.

The graphs on the right sides of FIGS. 11A and 11B illustrate the relationships, between the brightness command signals and the light source control signals, stored in the light control tables 36d and 37d for the third special mode, respectively. Based on the light control tables 36d and 37d, the two light source control signals n which correspond to the LEDs 24 and 25 are determined, respectively, relative to the single brightness command signal n. As shown by the graphs on the left sides of FIGS. 11A and 11B, the LEDs 24 and 25 emit the light with the light amounts LSB4 and LSC4 in response to the two light source control signals n, respectively. The light amount ratio between the light of the two colors substantially coincides with the predetermined set light amount ratio X4. The light amount ratio between the light of the two colors maintains itself substantially at the set light amount ratio X4 regardless of the value of the brightness command signal n.

The control signal correction table 43 is the same as that stored in the LUT 36 in the normal mode. In the control signal correction table 44, the relationships between the light source control signals and the corrected light source control signals (the light source control signals for linearly changing the light amount) also differ between the case where the light source control signal is less than or equal to the given value P* and the case where the light source control signal is greater than the given value P*, in a manner similar to the control signal correction tables 39 to 43.

As shown in FIG. 6A, the calibration circuit 30 comprises a calibration data generating unit 45, a light control table generating unit 46, and a test emission control unit 47. The calibration data generating unit 45 generates calibration data that describes relationships between the light amounts of the LEDs 20 to 25 and the light source control signals. The light control table generating unit 46 generates the light control tables used in the respective modes. The test emission control unit 47 controls the emissions of the LEDs 20 to 25 based on the light control tables and allows each of the LEDs 20 to 25 to perform a test emission, and determines whether the light amount of the test emission reaches a target light amount.

The calibration data generating unit 45 has a calibration light controller 45a and an associating section 45b (first associating section). Based on a predetermined calibration emission sequence, the calibration light controller 45a transmits the light source control signals to the LEDs 20 to 25 to control the emission conditions of the LEDs 20 to 25. First, the calibration light controller 45a transmits the light source control signal to the B-LED 20 to allow the B-LED 20 to emit the blue light B. The blue light B is applied to an integrating sphere ST (see FIG. 1), being a reference object. An image of the integrating sphere ST is captured with the image sensor 51c of the endoscope 12. Based on the image signal obtained with the image sensor 51c, a light amount calculator 55 in the processor device calculates the light amount of the blue light B. The calculated light amount of the blue light B is transmitted to the associating section 45b. Note that a white plate may be used instead of the integrating sphere ST.

During the application (emission) of the blue light B, the number of bits (hereinafter referred to as the bit number) of the light source control signal is incremented by one bit from "1" (the minimum bit) to "M" (the maximum bit) to gradually increase the intensity and the emission time of the blue light B. The light amount calculator 55 in the processor device calculates the light amount of the blue light B every time the bit number is incremented by one bit. After the light source control signal with the maximum bit number "M" is transmitted to the B-LED 20, the light source control signal with the minimum bit is transmitted to the G-LED 21 to allow the G-LED 21 to emit the green light G. The bit number M of the light source control signal is incremented by one bit, in a manner similar to the B-LED 20. Subsequently, the R-LED 22, the first special light LED 23, the second special light LED 24, and the third special light LED 25 are controlled in a manner similar to the B-LED 20. The light amount of each light is calculated every time the bit number is incremented by one bit.

The associating section 45b associates the light source control signal m, which is transmitted to the B-LED 20, with the light amount LB[m] (the light amount calculated by the light amount calculator 55 in the processor device) of the blue light B emitted from the B-LED 20 in response to the light source control signal m. Thereby the associating section 45b generates calibration data LPB[m] as shown in FIG. 12. The associating section 45b associates the light source control signals m transmitted to the G-LED 21, the R-LED 22, the first special light LED 23, the second special light LED 24, and the third special light LED 25 with the light amounts LG[m], LR[m], LSA[m], LSB[m], and LSC[m] of the light of the respective colors emitted from the LEDs 21 to 25 in response to the light source control signals m, respectively. Thereby the associating section 45b generates the calibration data LPG[m], LPR[m], LPSA[m], LPSB[m], and LPSC[m].

The light control table generating unit 46 comprises a maximum light amount setter 46a, an nth light amount setter 46b, a light source control signal setter 46c for the brightness step n (hereinafter, simply referred to as the light source control signal setter 46c), and an associating section 46d (second associating section). Based on the calibration data, the maximum light amount setter 46a sets the maximum light amount of the light used in each observation mode. As shown by the set light amount ratio X1 in FIG. 5, the light amount LB1 of the blue light is the highest of those of the blue light B, the green light G, the red light R, the first special light SA, and the second special light SB which are used in the normal mode. The highest light amount of the calibration data LPB[m] is set as the maximum light amount B1max of the blue light B.

The maximum light amounts G1max, R1max, SA1max, and SB2max of the green light G, the red light R, the first special light SA, and the second special light SB are set in accordance with the set light amount ratio X1, with the use of the maximum light amount B1max of the blue light B as a reference. The maximum light amount G1max of the green light G is set as B1max×(LG1/LB1). The maximum light amount R1max of the red light R is set as B1max×(LR1/LB1). The maximum light amount SA1max of the first special light SA is set as B1max×w1%. The maximum light amount SB1max of the second special light SB is set as B1max×w2%.

As shown by a set light amount ratio X2 in FIG. 5, the light amount LSA2 of the first special light SA is the highest of those of the green light G, the first special light SA, and the second special light SB which are used in the first special mode. The highest light amount of the calibration data LPSA[m] is set as the maximum light amount SA2max of the first special light SA1. Upon the setting of the maximum light amount SA2max of the first special light SA1, the maximum light amount G2max of the green light G is set as SA2max× (LG2/LSA2). The maximum light amount SB2max of the second special light SB is set as SA2max×t1%.

As shown by the set light amount ratio X3 in FIG. 5, in the second special mode, the light amount LSA3 of the first special light SA is the highest of the light amounts of the green light G, the red light R, the first special light SA, and the second special light SB which are used in the second special mode. The highest light amount of the calibration data LPSA[m] is set as the maximum light amount SA3max of the first special light SA. Upon the setting of the maximum light amount SA3max of the first special light SA, the maximum light amount R3max of the red light R is set as SA3max×(LR3/LSA3). The maximum light amount G3max of the green light G is set as SA3max×(LG3/LSA3). The maximum light amount SB3max of the second special light SB is set as SA3max×t2%.

As shown by the set light amount ratio X4 in FIG. 5, in the third special mode, the light amount of the third special light SC is set higher than the light amount of the second special light SB, so that the highest light amount of the calibration data LPSC[m] is set as the maximum light amount SC4max of the third special light SC. Upon the setting of the maximum light amount SC4max of the third special light SC, the maximum light amount SB4max of the second special light SB is set as SC4max×(SB4/SC4).

Based on the maximum (highest) light amount set by the maximum light amount setter 46a, the nth light amount setter 46b sets an nth light amount for the brightness step n. An nth light amount LB1[n] for the brightness step n of the blue light B used in the normal mode is calculated by dividing the maximum light amount B1max of the blue light B by N in a linear-antilogarithmic manner (LB1[n]=n×B1max/(N−1)). Nth light amounts LG1[n], LR1[n], LSA1[n], and LSB1[n], each corresponding to the brightness step "n", of the green light G, the red light R, the first special light SA, and the second special light SB for the normal mode are calculated in a similar manner. As shown by mathematical expressions 1-1, each of the maximum light amounts G1max, R1max, SA1max, and SB1max is divided by N in the linear-antilogarithmic manner. "Dividing the maximum light amount by N in a linear-antilogarithmic manner" is to multiply a value (the result of dividing the maximum light amount, being the antilogarithm, by N−1) by a coefficient n of the brightness step n. Thereby, the nth light amount increases or decreases linearly relative to the brightness step n.

$$LG1[n]=n\times G1\mathrm{max}/(N-1)$$

$$LR1[n]=n\times R1\mathrm{max}/(N-1)$$

$$LSA1[n]=n\times SA1\mathrm{max}/(N-1)$$

$$LSB1[n]=n\times SB1\mathrm{max}/(N-1) \quad \text{(Mathematical expressions 1-1)}$$

Note that each of the nth light amounts LB1[n], LG1[n], LR1[n], LSA1[n], and LSB1[n] may be calculated by dividing each of the maximum light amounts B1max, G1max, R1max, SA1max, and SB1max by N in a linear-logarithmic manner as shown by mathematical expressions 1-2 below. "Dividing the maximum light amount by N in a linear-logarithmic manner" is to logarithmize a value (the result of dividing the maximum light amount, being the antilogarithm, by N−1), and multiply a value (powers of 10 with an exponent, being the logarithmized value) by a coefficient n of the brightness step n. Thereby the nth light amount increases or decreases linearly relative to the brightness step n.

$$LB1[n]=n\times 10^{\wedge}(\log(B1\mathrm{max})/(N-1))$$

$$LG1[n]=n\times 10^{\wedge}(\log(G1\mathrm{max})/(N-1))$$

$$LR1[n]=n\times 10^{\wedge}(\log(R1\mathrm{max})/(N-1))$$

$$LSA1[n]=n\times 10^{\wedge}(\log(SA1\mathrm{max})/(N-1))$$

$$LSB1[n]=n\times 10^{\wedge}(\log(SB1\mathrm{max})/(N-1)) \quad \text{(Mathematical expressions 1-2)}$$

Nth light amounts LG2[n], LSA2[n], and LSB2[n] (for the brightness step n) of the green light G, the first special light SA, and the second special light SB, which are used in the first special mode, are calculated in the manner similar to the above. As shown by mathematical expressions 2 below, each of the maximum light amounts G2max, SA2max, and SB2max is divided by N in the linear-antilogarithmic manner (or the linear-logarithmic manner).

$$LG2[n]=n\times G2\mathrm{max}/(N-1)$$

$$LSA2[n]=n\times SA2\mathrm{max}/(N-1)$$

$$LSB2[n]=n\times SB2\mathrm{max}/(N-1) \quad \text{(Mathematical expressions 2)}$$

Nth light amount LG3[n], LR3[n], LSA3[n], and LSB3[n] (for the brightness step n) of the green light G, the red light R, the first special light SA, and the second special light SB, which are used in the second special mode, are calculated in the manner similar to the above. As shown by mathematical expressions 3 below, each of the maximum light amounts G3max, R3max, SA3max, and SB3max is divided by N in the linear-antilogarithmic manner (or the linear-logarithmic manner).

$$LG3[n]=n\times G3\mathrm{max}/(N-1)$$

$$LR3[n]=n\times G3\mathrm{max}/(N-1)$$

$$LSA3[n]=n\times SA3\mathrm{max}/(N-1)$$

$$LSB3[n]=n\times SB3\mathrm{max}/(N-1) \quad \text{(Mathematical expressions 3)}$$

Nth light amounts LSB4[n] and LSC4[n] (for the brightness step n) of the second special light SB and the third special light SC, which are used in the third special mode, are calculated in the manner similar to the above. As shown by mathematical expressions 4 below, each of the maximum light amounts SB4max and SC4max is divided by N in the linear-antilogarithmic manner (or the linear-logarithmic manner).

$$LSB4[n]=n\times SB4\mathrm{max}/(N-1)$$

$$LSC4[n]=n\times SC4\mathrm{max}/(N-1) \quad \text{(Mathematical expressions 4)}$$

The light source control signal setter 46c refers to the calibration data and determines the light amounts which are closest to the nth light amounts of the respective colors, which are obtained by the nth light amount setter 46b. The light source control signal setter 46c sets the light source control signals, which are associated with the determined light amounts, as the light source control signals for the brightness step n (hereinafter simply referred to as the brightness step n light source control signals). The brightness step n light source control signals are set for each observation mode.

In the normal mode, the B-LED 20, the G-LED 21, the R-LED 22, the first special light LED 23, and the second special light LED 24 are turned on, so that the calibration data LPB[m], LPG[m], LPR[m], LPSA[m], and LPSB[m], which correspond to the LEDs 20 to 24 of these five colors, are used for setting the brightness step n light source control signals (the light source control signals for the brightness step n), respectively. First, referring to the calibration data LPB[m], the light source control signal setter 46c determines the light amount closest to the nth light amount LB1[n] of the blue light B set by the nth light amount setter 46b. The light source control signal setter 46c determines the light source control signal which is associated with the determined light amount from the calibration data LPB[m], and sets the determined light source control signal as the brightness step n light source control signal (light source control signal n for the brightness step n) which is used for the emission control of the B-LED 20 in the normal mode. The brightness step n light source control signals which are used for the emission control (for the normal mode) of the G-LED 21, the R-LED 22, the first special light LED 23, and the second special light LED 24 are determined based on the calibration data LPG[m], LPR[m], LPSA[m], and LPSB[m], respectively, in a manner similar to the above.

In the first special mode, the G-LED 21, the first special light LED 23, and the second special light LED 24 are turned on, so that the calibration data LPG[m], LPSA[m], and LPSB[m], which correspond to the LEDs 21, 23, and 24 of the three colors, are used for setting the brightness step n light source control signals (light source control signals n for the brightness step n), respectively. First, referring to the calibration data LPG[m], the light source control signal setter 46c determines the light amount closest to the nth light amount LG2[n] of the green light G (for the first special mode) set by the nth light amount setter 46b. The light source control signal setter 46c determines the light source control signal which is associated with the determined light amount from the calibration data LPG[m], and sets the determined light source control signal as the brightness step n light source control signal (light source control signal n for the brightness step n) which is used for the emission control of the G-LED 21 in the first special mode. The brightness step n light source control signals which are used for the emission control of the first special light LED 23 and the second special light LED 24 are determined based on the calibration data LPSA[m] and LPSB[m], respectively, in a manner similar to the above.

In the second special mode, the G-LED 21, the R-LED 22, the first special light LED 23, and the second special light LED 24 are turned on, so that the calibration data LPG[m], LPR[m], LPSA[m], and LPSB[m], which correspond to the LEDs 21 to 24 of the four colors, are used for setting the brightness step n light source control signals (light source control signals for the brightness step n), respectively. First, referring to the calibration data LPG[m], the light source control signal setter 46c determines the light amount closest to the nth light amount LG3[n] of the green light G (for the second special mode) set by the nth light amount setter 46b. The light source control signal setter 46c determines the light source control signal which is associated with the determined light amount from the calibration data LPB[m], and sets the determined light source control signal as the brightness step n light source control signal (light source control signal n for the brightness step n) which is used for the emission control of the G-LED 21 in the second special mode. The brightness step n light source control signals which are used for the emission control (for second special mode) of the R-LED 22, the first special light LED 23, and the second special light LED 24 are determined based on the calibration data LPR[m], LPSA[m], and LPSB[m], respectively, in a manner similar to the above.

In the third special mode, the second special light LED 24 and the third special light LED 25 are turned on, so that the calibration data LPSB[m] and LPSC[m], which correspond to the LEDs 24 and 25 of the two colors, are used for setting the brightness step n light source control signals (light source control signals n for the brightness step n), respectively. First, referring to the calibration data LPSB[m], the light source control signal setter 46c determines the light amount closest to the nth light amount LSB4[n] of the second special light SB (for the third special mode) set by the nth light amount setter 46b. The light source control signal setter 46c determines the light source control signal which is associated with the determined light amount from the calibration data LPSB[m], and sets the determined light source control signal as the brightness step n light source control signal (light source control signal n for the brightness step n) which is used for the emission control of the second special light LED 24 in the third special mode. The brightness step n light source control signal which is used for the emission control (for third special mode) of the third special light LED 25 is determined based on the calibration data LPSC[m], in a manner similar to the above.

The associating section 46d associates the brightness step n light source control signal (the light source control signal n for the brightness step n), which is set by the light source control signal setter 46c, with the brightness command signal n for the brightness step n, and thereby generates the light control table for each observation mode. As for the light control table for the normal mode, first, the associating section 46d associates the brightness step n light source control signal (the light source control signal n for the brightness step n for the B-LED 20), which is set by the light source control signal setter 46c, with the brightness command signal n, which corresponds to the brightness step n. Thus, the associating section 46d generates the B1 light control table (see FIG. 13). The G1 light control table, the R1 light control table, the SA1 light control table, and the SB2 light control table are formed in a manner similar to the B1 light control table.

As for the light control table for the first special mode, the associating section 46d associates the brightness step n light source control signal (the light source control signal n for the brightness step n for the G-LED 21), which is set by the light source control signal setter 46c, with the brightness command signal n, which corresponds to the brightness step n. Thus, the associating section 46d generates the G2 light control table. The SA2 light control table and the SB2 light control table are generated in a manner similar to the G2 light control table.

As for the light control table for the second special mode, the G3 light control table is generated by associating the brightness step n light source control signal (the light source control signal n for the brightness step n for the G-LED 21), which is set by the light source control signal setter 46c, with the brightness command signal n, which corresponds to the brightness step n. The R3 light control table, the SA3 light control table, and the SB3 light control table are generated in a manner similar to the G3 light control table.

As for the light control table for the third special mode, the SB4 light control table is generated by associating the brightness step n light source control signal (the light source control signal n for the brightness step n for the second special light LED 24), which is set by the light source control signal setter 46c, with the brightness command signal n, which corresponds to the brightness step n. Thus, the associating section 46d generates the SB4 light control table. The SC4 light control table is generated in a manner similar to the SB4 light control table.

The test emission control unit 47 controls the light emissions of the LEDs 20 to 25 based on the respective light control tables, which are generated in the light control table generating unit 46. Thereby, the test emission control unit 47 allows the LEDs 20 to 25 to perform the test emissions. The test emissions include the test emissions for the normal mode based on the light control tables 32a to 36a for the normal mode, the test emissions for the first special mode based on the light control tables 33b, 35b, and 36b for the first special mode, the test emissions for the second special mode based on the light control tables 33c to 36c for the second special mode, and the test emissions for the third special mode based on the light control tables 36d and 37d for the third special mode.

As for the test emission for the normal mode, a given brightness command signal n* is inputted to the B1 light control table 32a. Thereby the blue light B (for the brightness step n*) which corresponds to the brightness command signal n* is emitted. The light amount calculator 55 in the processor device calculates the light amount of the blue light B emitted.

The calculated light amount is transmitted to the test emission control unit 47. The test emission control unit 47 calculates an error ΔBE1 between the light amount calculated by the light amount calculator 55 and the target light amount (for the blue light B) which corresponds to the brightness step n*. In a manner similar to the above, the given brightness command signal n* is inputted to each of the G1 light control table 33a, the R1 light control table 34a, the SA1 light control table 35a, and the SB1 light control table 36a. Thereby the green light G, the red light R, the first special light SA, and the second special light SB, each corresponding to the brightness step n*, are emitted. The test emission control unit 47 calculates errors ΔGE1, ΔRE1, ΔSAE1, and ΔSBE1, between the light amount of each color and the target light amount. Note that the target light amount (for the blue light B) for the brightness step n* corresponds to the nth light amount LB1[n*] (for the blue light B), which corresponds to the brightness step n*, set by the nth light amount setter 46b. The same holds true for the rest of the target light amounts. The nth light amounts are set by the nth light amount setter 46b.

In a case where the errors satisfy ΔBE1≈ΔGE1≈ΔRE1≈ΔSAE1≈ΔSBE1 and these errors of the light of the five colors are substantially "0", it is determined that the light amount ratio among the light of the five colors coincides with the set light amount ratio X1 regardless of the value of the brightness command signal n. In this case, regeneration of the light control tables 32a, 33a, 34a, 35a, and 36a is not performed. The light control tables 32a, 33a, 34a, 35a, and 36a are regenerated in a case where at least one of the errors ΔGE1, ΔRE1, ΔSAE1, and ΔSBE1 is out of a certain range.

The light control table regenerator 47a performs a regeneration process of the light control tables as follows, by way of example. In a case where the error ΔRE of the red light R is the largest of the errors of the light of the five colors, the light amount of the red light R, calculated by the light amount calculator 55, is reset as the light amount for the brightness step n*, which is used as the reference light amount. The light amounts of the blue light B, the green light G, the first special light SA, and the second special light SB are reset in accordance with the set light amount ratio X1 as follows: the light amount of the blue light B=the reference light amount×(B1/R1); the light amount of the green light G=the reference light amount×(G1/R1); the light amount of the first special light SA=the reference light amount×(SA1/R1); the light amount of the second special light SB=the reference light amount× (SB1/R1).

Then, referring to the calibration data LPR[m], the light source control signal which corresponds to the reset light amount of the red light R for the brightness step n* is selected. In the R1 light control table 34a, the selected light source control signal is reassociated with the brightness command signal for the brightness step n*. Referring to the calibration data LPB[m], LPG[m], LPSA[m], and LPSB[m], the light source control signals which correspond to the reset light amounts of the blue light B, the green light G, the first special light SA, and the second special light SB (for the brightness step n*) are selected, respectively. Based on the selected light source control signals, the blue light B, the green light G, the first special light SA, and the second special light SB are emitted and the light amounts thereof are calculated, respectively. Thereby the errors ΔBE2, ΔGE2, ΔSAE2, and ΔSBE2 are calculated. The errors ΔBE1, ΔGE1, ΔSAE1, and ΔSBE1 are compared with the errors ΔBE2, ΔGE2, ΔSAE2, and ΔSBE2, respectively. The light amount with the error smaller than the other is selected.

In a case where the errors ΔGE2, ΔSAE2, and ΔSBE2 are smaller than the errors ΔGE1, ΔSAE1, and ΔSBE1, the light source control signals which correspond to the reset light amounts (for the brightness step n*) of the green light G, the first special light SA, and the second special light SB are reassociated with the brightness command signals (for the brightness step n*) in the G1 light control table 33a, the SA1 light control table 35a, and the SB1 light control table 36a, respectively. In a case where the error ΔBE2 is greater than the error ΔBE1, the brightness command signal for the brightness step n* in the B1 light control table 32a is not changed.

Note that the test emission for the first special mode, the test emission for the second special mode, and the test emission for the third special mode are performed in a manner similar to the test emission for the normal mode.

As shown in FIG. 2, the distal portion 12d of the endoscope 12 has an illumination optical system 50 and an imaging optical system 51. The illumination optical system 50 has the lighting lens 50a. The light from the light guide 49 is applied to the observation object through the lighting lens 50a. The imaging optical system 51 has an objective lens 51a, the zooming lens 51b, and the image sensor 51c. The reflection light from the observation object is incident on the image sensor 51c through the objective lens 51a and the zooming lens 51b. Thereby a reflection image of the observation object is formed on the image sensor 51c.

The image sensor 51c is a color image sensor. The image sensor 51c captures the reflection image of the observation object, and outputs an image signal. It is preferred that the image sensor 51c is a CCD (Charge Coupled Device) image sensor, a CMOS (Complementary Metal-Oxide Semiconductor) image sensor, or the like. The image sensor used in the present invention is a color image sensor for obtaining image signals of three colors, R (red), G (green), and B (blue), that is, the so-called RGB image sensor provided with RGB filters in an imaging surface. Here, a pixel provided with the R filter is referred to as the R pixel. A pixel provided with the G filter is referred to as the G pixel. A pixel provided with the B filter is referred to as the B pixel.

Note that the image sensor 51c may be a so-called complementary color image sensor instead of the RGB image sensor. The complementary color image sensor has complementary color filters of C (cyan), M (magenta), Y (yellow), and G (green) with spectral transmittance. In the case where the complementary color image sensor is used, the image signals of four colors (CMYG) are color-converted into the image signals of three colors (RGB). In this case, one of the endoscope 12 or the processor device 16 is provided with a color converting means for color-converting the image signals of four colors (CMYG) into the image signals of three colors (RGB).

The image signal outputted from the image sensor 51c is transmitted to a CDS/AGC circuit 52. The CDS/AGC circuit 52 performs correlated double sampling (CDS) and automatic gain control (AGC) on the image signal, being an analog signal. The image signal which has passed through the CDS/AGC circuit 52 is converted into a digital image signal by an A/D converter 53. The A/D converted digital image signal is inputted to the processor device 16.

The processor device 16 comprises a receiver 54, the light amount calculator 55, a DSP (digital signal processor) 56, a noise remover 58, a brightness command signal generator 59, an image processing selector 60, a normal image processor 62, a first special image processor 63, a second special image processor 64, a third special image processor 65, and a video signal generator 66. The receiver 54 receives the digital RGB image signals from the endoscope 12. The light amount calculator 55 calculates the light amount of each illumination light based on the digital image signals received by the receiver 54. In the normal mode or the special mode, the calculated light amount is transmitted to the brightness command signal generator 59. In the calibration mode, the calculated light amount is transmitted to the calibration circuit 30 of the light source device.

The brightness command signal generator 59 calculates a target light amount based on the light amount calculated by the light amount calculator 55, and calculates the brightness command signal n based on the calculated target light amount. The target light amount increases with the number of bits of the brightness command signal n. The generated brightness command signal n is transmitted to the observation circuit 29 of the light source device.

The DSP 56 performs gamma correction and color correction process on the image signal received by the receiver 54. Thereafter, the noise remover 58 removes noise from the image signal through a noise removing process (for example, method of moving average or median filter method). Then, the image signal is transmitted to the image processing selector 60.

In the normal mode, the image processing selector 60 transmits the RGB image signals to the normal image processor 62. In the first special mode, the image processing selector 60 transmits the RGB image signals to the first special image processor 63. In the second special mode, the image processing selector 60 transmits the RGB image signals to the second special image processor 64. In the third special mode, the image processing selector 60 transmits the RGB image signals to the third special image processor 65. The observation mode is switched through the operation of the mode SW 13$a$.

The normal image processor 62 produces the normal image in which the observation object is displayed in normal (actual) colors of tissue. The first special image processor 63 produces a first special image in which blood vessels or the like on the observation object are enhanced. The second special image processor 64 produces a second special image in which the blood vessels or the like on the observation object are enhanced and the brightness is maintained substantially the same as that of the normal image. The third special image processor 65 produces a third special image in which oxygen saturation levels of hemoglobin in blood of the observation object are displayed in pseudo color. The images produced in the image processors 62 to 65 are transmitted to the video signal generator 66.

Note that each of the image processors 62 to 65 preferably comprises a color converter, a gradation converter, a color enhancer, and a structure enhancer. The color converter performs a color conversion process on the RGB image signals. The gradation converter performs a gradation conversion process on color-converted image signals. The color enhancer performs various color enhancement processes on gradation-converted image signals. The structure enhancer performs structure enhancement processes such as sharpness enhancement and edge enhancement on color-enhanced image signals.

The video signal generator 66 converts the image inputted from each of the image processors 62 to 65 into a video signal to display the image on the monitor 18. Based on the video signal, the monitor 18 displays the normal image in the normal mode, the first special image in the first special mode, the second special image in the second special mode, or the third special image in the third special mode.

Figure 14:
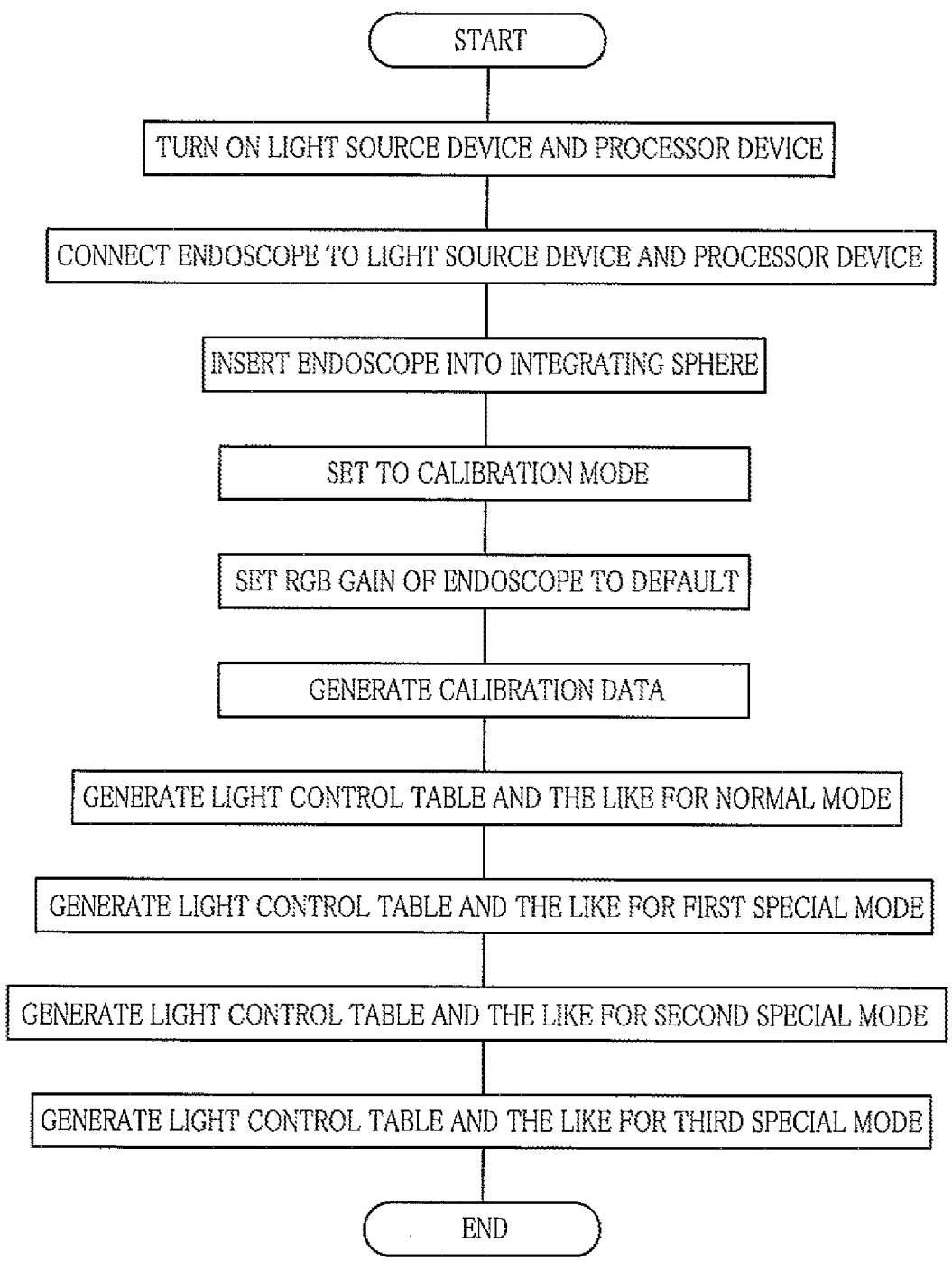
FIG. 14 is a flowchart illustrating a calibration method according to the present invention.

Next, referring to a flowchart in FIG. 14, a calibration method of the present invention is described. First, the light source device 14 and the processor device 16 are turned on.

The endoscope 12 is connected to the light source device 14 and the processor device 16. The distal portion 12$d$ of the endoscope 12 is inserted into the integrating sphere ST, being the reference object. The mode SW 13$a$ is operated to set the observation mode to the calibration mode. The console 19 is operated to set the RGB gain of the image sensor 51$c$ of the endoscope 12 to the default.

Then, the calibration data is generated. First, the calibration light controller 45$a$ of the calibration data generating unit 45 is activated to perform the calibration emission sequence. In the calibration emission sequence, the light source control signal is applied to each of the B-LED 20, the G-LED 21, the R-LED 22, the first special light LED 23, the second special light LED 24, and the third special light LED 25 to emit the blue light B, the green light G, the red light R, the first special light SA, the second special light SB, and the third special light SC in this order. The light amount calculator 55 measures the light amount of each light. Next, the associating section 45$b$ associates the light source control signals transmitted to the LEDs 20 to 25 with the light amounts of the light emitted in response to the transmitted light source control signals, respectively, and thereby generates the calibration data LPB[m], LPG[m], LPR[m], LPSA[m], LPSB[m], and LPSC[m].

Figure 15:
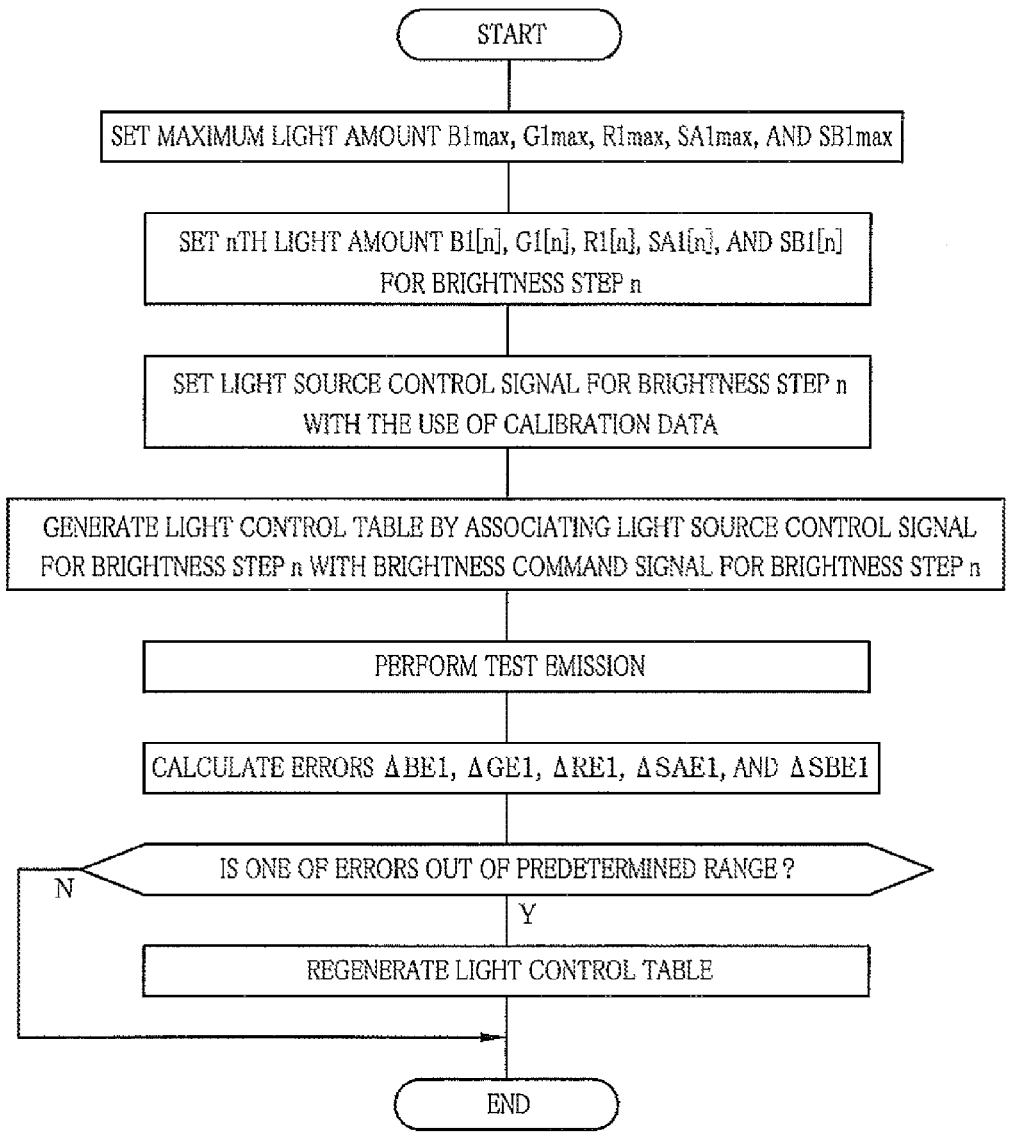
FIG. 15 is a flowchart illustrating a method for generating a light control table for a normal mode.

Then, a step for generating the light control tables for the normal mode is performed. In the normal mode, the B-LED 20, the G-LED 21, the R-LED 22, the first special light LED 23, and the second special light LED 24 are turned on, so that the light control tables are generated using the calibration data LPB[m], LPG[m], LPR[m], LPSA[m], and LPSB[m], respectively. First, as shown by a flowchart in FIG. 15, the maximum light amount setter 46$a$ sets the maximum light amounts B1max, G1max, R1max, SA1max, and SB1max of the blue light B, the green light G, the red light R, the first special light SA, and the second special light SB, respectively. The maximum light amount B1max of the blue light B, which is the highest of the light amounts of the light of these five colors, is set as the highest light amount of the calibration data LPB[m]. The maximum light amounts G1max, R1max, SA1max, and SB1max are set based on the maximum light amount B1max of the blue light B and the set light amount ratio X1.

Based on the maximum light amounts B1max, G1max, R1max, SA1max, and SB1max set by the maximum light amount setter 46$a$, the nth light amount setter 46$b$ sets the nth light amounts LB1[n], LG1[n], LR1[n], LSA1[n], and LSB1[n] for the brightness step n. Next, the light source control signal setter 46$c$ refers to the calibration data LPB[m], LPG[m], LPR[m], LPSA[m], and LPSB[m] to determine the light amounts closest to the nth light amounts LB1[n], LG1[n], LR1[n], LSA1[n], and LSB1[n], respectively. The light source control signal setter 46$c$ sets the light source control signals which are associated with the light amounts determined to be closest to the nth light amounts LB1[n], LG1[n], LR1[n], LSA1[n], and LSB1[n], as the brightness step n light source control signals (the light source control signals for the brightness step n).

The associating section 46$d$ associates the brightness step n light source control signals (the light source control signals for the brightness step n), which have been set by the light source control signal setter 46$c$, with the brightness command signal n for the brightness step n. Thereby, the B1 light control table 32$a$, the G1 light control table 33$a$, the R1 light control table 34$a$, the SA1 light control table 35$a$, and the SB1 light control table 36$a$, which are for the normal mode, are obtained.

Next, the test emission control unit 47 performs the test emissions of the LEDs 20 to 24 based on the respective light control tables 32a to 36a. First, the predetermined brightness command signal n* is inputted to the light control table 32a to perform the test emission of the blue light B. Then, an error between the light amount of the test-emitted blue light B and the target light amount is calculated as an error $\Delta BE'$. The test emissions are performed for the light control tables 33a to 36a, and errors $\Delta GE1$, $\Delta RE1$, $\Delta SAE1$, and $\Delta SBE1$ from the target light amounts are calculated, respectively, in a manner similar to the above.

The light control tables 32a to 36a are not regenerated in a case where $\Delta BE1 \approx \Delta GE1 \approx \Delta RE1 \approx \Delta SAE1 \approx \Delta SBE1$ and the values of these errors are substantially "0". The light control tables 32a to 36a are regenerated in a case where at least one of the errors $\Delta GE1$, $\Delta RE1$, $\Delta SAE1$, and $\Delta SBE1$ is out of a certain range. The light control table regenerator 47a performs a regeneration process of the light control tables. The regenerated light control tables replace the immediately preceding light control tables.

The light control tables 32a to 36a are joined to the B control signal correction table 39, the G control signal correction table 40, the R control signal correction table 41, the SA control signal correction table 42, and the SB control signal correction table 43 to generate the joint tables TB1, TG1, TR1, TSA1, and TSB1, respectively. The joint tables TB1, TG1, TR1, TSA1, and TSB1 are stored in the memory 31.

Next, a step for generating the light control tables for the first special mode is described. In the first special mode, the G-LED 21, the first special light LED 23, and the second special light LED 24 are turned on, so that the calibration data LPG[m], LPSA[m], and LPSB[m] are used to generate the light control tables, respectively. The light control table generating unit 46 generates the light control tables 33b, 35b, and 36b, based on the calibration data LPG[m], LPSA[m], and LPSB[m], respectively. After the light control tables are generated, the test emission control unit 47 performs the test emissions. In a case where the error between the light amount of the test emission and the target light amount is out of the predetermined range, the light control table regenerator 47a regenerates the light control table(s).

The light control tables 33b, 35b, and 36b are joined to the G control signal correction table 40, the SA control signal correction table 42, and the SB control signal correction table 43 to generate the joint tables TG2, TSA2, and TSB2, respectively. The joint tables TG2, TSA2, and TSB2 are stored in the memory 31.

Next, a step for generating the light control tables for the second special mode is described. In the second special mode, the G-LED 21, the R-LED 22, the first special light LED 23, and the second special light LED 24 are turned on, so that the calibration data LPG[m], LPR[m], LPSA[m], and LPSB[m] are used to generate the light control tables, respectively. The light control table generating unit 46 generates the light control tables 33c, 34c, 35c, and 36c based on the calibration data LPG[m], LPR[m], LPSA[m], and LPSB[m], respectively. The generated light control tables 33c, 34c, 35c, and 36c are stored in the memory 31 in the light source controller. After the light control tables are generated, the test emission control unit 47 performs the test emissions. In a case where the error between the light amount of the test emission and the target light amount is out of the predetermined range, the light control table regenerator 47a regenerates the light control table(s).

The light control tables 33c to 36c are joined to the G control signal correction table 40, the R control signal correction table 41, the SA control signal correction table 42, and the SB control signal correction table 43, to generate the joint tables TG3, TR3, TSA3, and TSB3, respectively. The joint tables TG3, TR3, TSA3, and TSB3 are stored in the memory 31.

Next, a step for generating the light control tables for the third special mode is described. In the third special mode, the second special light LED 24 and the third special light LED 25 are turned on, so that the calibration data LPSB[m] and LPSC[m] are used to generate the light control tables. The light control table generating unit 46 generates the light control tables 36d and 37d based on the calibration data LPSB[m] and LPSC[m], respectively. The generated light control tables 36d and 37d are stored in the memory 31 of the light source controller. After the light control tables are generated, the test emission control unit 47 performs the test emissions. In a case where the error between the light amount of the test emission and the target light amount is out of the predetermined range, the light control table regenerator 47a regenerates the light control table(s).

The light control tables 36d and 37d are joined to the SB control signal correction table 43 and the SC control signal correction table 44 to generate the joint tables TSB4 and TSC4, respectively. The joint tables TSB4 and TSC4 are stored in the memory 31. Thereby, the calibration method of the present invention is completed. Note that the endoscope 12 is pulled out from the integrating sphere ST and the light source device 14 and the processor device 16 are turned off after the calibration is completed.

Figures 16, 17:
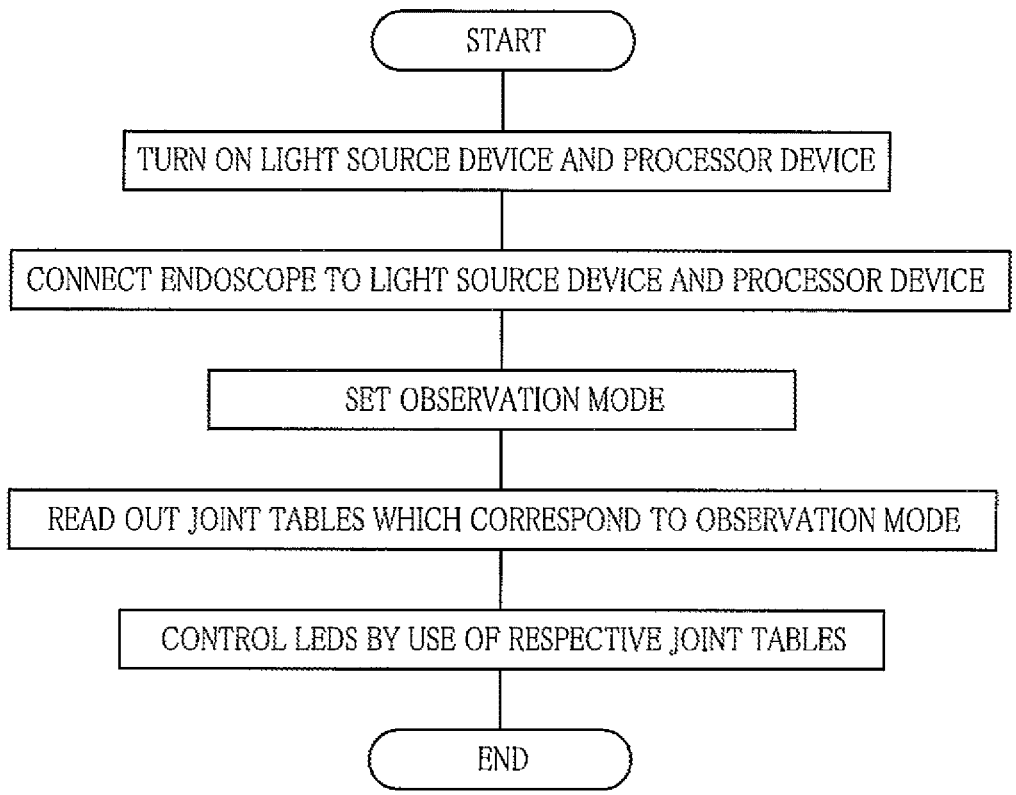
FIG. 16 is a flowchart illustrating a flow for observation of an observation object with the use of a joint table obtained by the calibration method according to the present invention.
FIG. 17 is a table illustrating a set signal ratio in each observation mode.

Next, referring to a flowchart in FIG. 16, the observation using the light control tables and the like obtained by the calibration method of the present invention is described. First, the light source device 14 and the processor device 16 are turned on. The distal portion 12d of the calibrated endoscope 12 is inserted into a body cavity. The mode SW 13a is operated to select and set the observation mode. Note that the endoscope is pulled out from the body cavity and the light source device 14 and the processor device 16 are turned off after the observation is ended.

In a case where the observation mode is set to the normal mode, the joint tables TB1, TG1, TR1, TSA1, and TSB1 are read out from the memory 31 of the light source device 14. The joint tables TB1, TG1, TR1, TSA1, and TSB1 are stored in the B-LUT 32, the G-LUT 33, the R-LUT 34, the first special light LUT 35, and the second special light LUT 36, respectively.

The light source controller 27 controls the emissions of the B-LED 20, the G-LED 21, the R-LED 22, the first special light LED 23, and the second special light LED 24 based on the LUTs 32 to 36, respectively. Thereby, the blue light B, the green light G, the red light R, the first special light SA, and the second special light SB are applied. The light amount ratio among the light of these five colors maintains itself at the set light amount ratio X1 regardless of the value of the brightness command signal n inputted to the light source controller 27. Since the LUTs 32 to 36 are used to correct the wavelength variations of the LEDs 20 to 24, respectively, the light amount ratio among the light of the five colors does not vary from the set light amount ratio X1 even if the emission intensities of the LEDs 20 to 24 are high.

In a case where the observation mode is set to the first special mode, the joint tables TG2, TSA2, and TSB2 are read out from the memory 31 of the light source device 14. The joint tables TG2, TSA2, and TSB2 are stored in the G-LUT 33, the first special light LUT 35, and the second special light LUT 36, respectively.

The light source controller 27 controls the emissions of the G-LED 21, the first special light LED 23, and the second special light LED 24 based on the LUTs 33, 35, and 36, respectively. Thereby, the green light G, the first special light SA, and the second special light SB are emitted. The light amount ratio among the light of these three colors maintains itself at the set light amount ratio X2 regardless of the value of the brightness command signal n inputted to the light source controller 27. Since the LUTs 33, 35, and 36 are used to correct the wavelength variations of the LEDs 21, 23, and 24, respectively, the light amount ratio among the light of the three colors does not vary from the set light amount ratio X2 even if the emission intensities of the LEDs 21, 23, and 24 are high.

In the second special mode, the joint tables TG3, TR3, TSA3, and TSB3 are read out from the memory 31 of the light source device 14. The joint tables TG3, TR3, TSA3, and TSB3 are stored in the G-LUT 33, the R-LUT 34, the first special light LUT 35, and the second special light LUT 36, respectively.

The light source controller 27 controls the emissions of the G-LED 21, the R-LED 22, the first special light LED 23, and the second special light LED 24 based on the LUTs 33 to 36, respectively. Thereby, the green light G, the red light R, the first special light SA, and the second special light SB are emitted. The light amount ratio among the light of these four colors maintains itself at the set light amount ratio X3 regardless of the value of the brightness command signal n inputted to the light source controller 27. Since the LUTs 33 to 36 are used to correct the wavelength variations of the LEDs 21 to 24, respectively, the light amount ratio among the light of the four colors does not vary from the set light amount ratio X3 even if the emission intensities of the LEDs 21 to 24 are high.

In the third special mode, the joint tables TSB4 and TSC4 are read out from the memory 31 of the light source device 14. The joint tables TSB4 and TSC4 are stored in the second special light LUT 36 and the third special light LUT 37, respectively.

The light source controller 27 controls the emissions of the second special light LED 24 and the third special light LED 25 based on the LUTs 36 and 37, respectively. Thereby, the second special light SB and the third special light SC are applied. The light amount ratio between the light of these two colors maintains itself at the set light amount ratio X4 regardless of the value of the brightness command signal n inputted to the light source controller 27. Since the LUTs 36 and 37 are used to correct the wavelength variations of the LEDs 24 and 25, the light amount ratio between the light of the two colors does not vary from the set light amount ratio X4 even if the emission intensities of the LEDs 24 and 25 are high.

Second Embodiment

In the first embodiment, the light control table allows the light amount ratio among the types of illumination light to coincide with the predetermined light amount ratio regardless of the value of the brightness command signal n. In the second embodiment, the signal ratio among the RGB image signals, which are obtained in a case where the observation object under different types of illumination light is imaged with the image sensor, is determined in advance as a set signal ratio. Then, a light control table is generated. The light control table allows the signal ratio among the RGB image signals (hereinafter simply referred to as the signal ratio) to coincide with the set signal ratio regardless of the value of the brightness command signal n. Other than that, the second embodiment is similar to the first embodiment.

In the second embodiment, as shown in FIG. 17, a set signal ratio is determined in advance for each observation mode. A set signal ratio r1:g1:b1 for the normal mode is a signal ratio among the RGB image signals which are obtained in a case where the light of the five colors (the blue light, the green light, the red light, the first special light, and the second special light) are applied to the observation object. A set signal ratio g2:b2 for the first special mode is a signal ratio between the G and B image signals which are obtained in a case where the light of the three colors (the green light, the first special light, and the second special light) are applied to the observation object. A set signal ratio r3:g3:b3 for the second special mode is a signal ratio among the RGB image signals which are obtained in a case where the light of the four colors (the green light, the red light, the first special light, and the second special light) are applied to the observation object. A set signal ratio g4:b4 for the third special mode is a signal ratio between the G and B image signals which are obtained in a case where the light of the two colors (the second special light and the third special light) are applied to the observation object.

Figure 18:
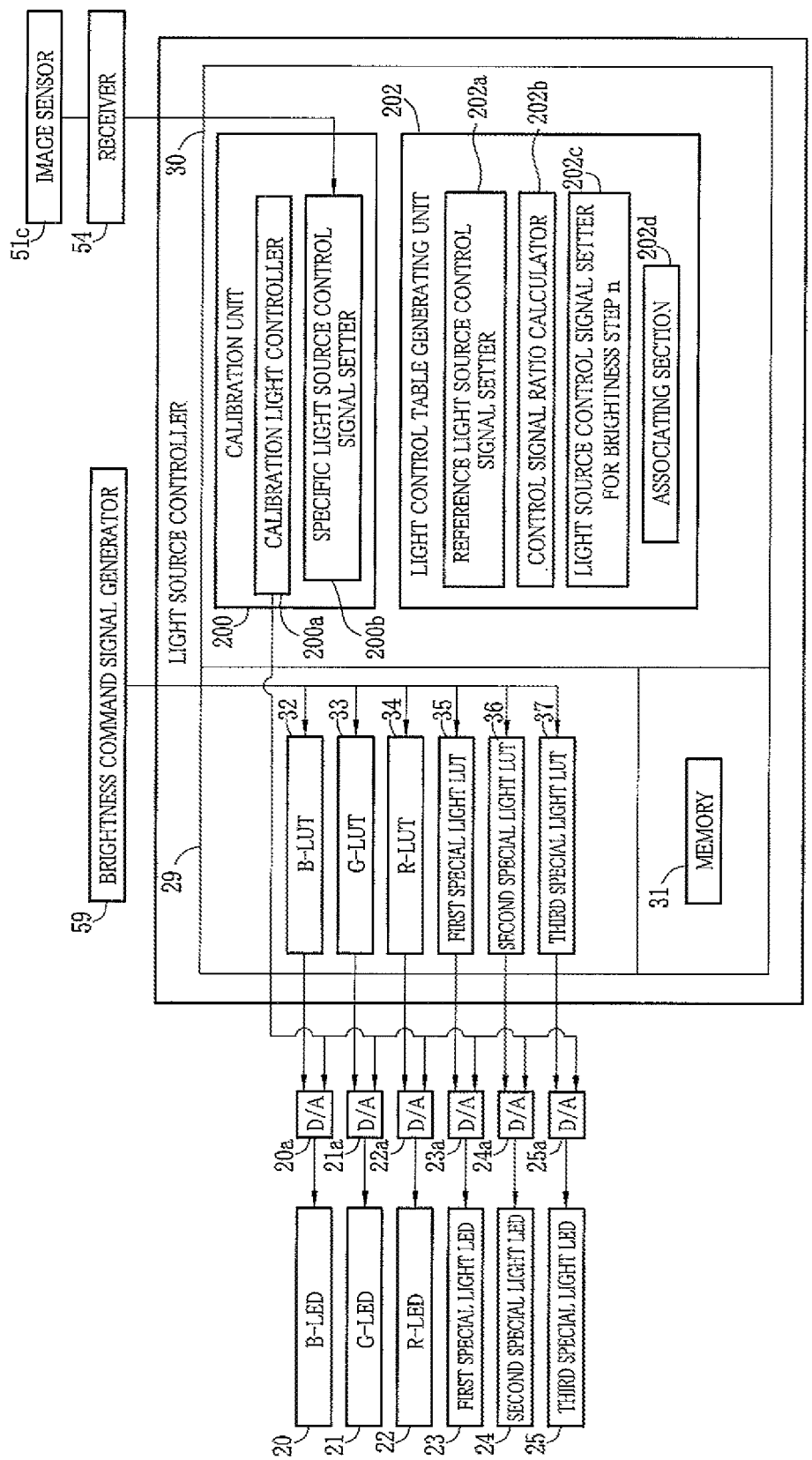
FIG. 18 is a block diagram illustrating functions of a light source controller in a second embodiment.

As shown in FIG. 18, the calibration circuit 30 of the light source controller 27 of the second embodiment is provided with a calibration unit 200 and a light control table generating unit 202, instead of the calibration data generating unit 45, the light control table generating unit 46, and the test emission control unit 47 of the first embodiment. The calibration unit 200 has a calibration light controller 200a and a specific light source control signal setter 200b.

The calibration unit 200 follows a calibration sequence determined for each observation mode. In a calibration sequence for the normal mode, the calibration light controller 200a is controlled to simultaneously turn on the five LEDs (the B-LED 20, the G-LED 21, the R-LED 22, the first special light LED 23, and the second special light LED 24). The blue light, the green light, the red light, the first special light, and the second special light from the respective LEDs 20 to 24 are applied to the integrating sphere ST. The image sensor 51c images the integrating sphere ST under the light of the five colors. Thereby the image sensor 51c outputs the RGB image signals.

The bit numbers of light source control signals VB[m], VG[m], VR[m], VSA[m], and VSB[m] applied to the respective LEDs 20 to 24 are changed from "M/2 (half the maximum bit number) to "M (the maximum bit number). Thereby the light intensity and the emission time of each of the blue light, the green light, the red light, the first special light, and the second special light from each of the LEDs are changed. Every time the bit number of the light source control signal changes, the image sensor 51c images the integrating sphere ST, and outputs the RGB image signals. Note that the bit number may be changed from, for example, "0" instead of M/2 (half the maximum bit number).

The specific light source control signal setter 200b determines whether the signal ratio among the RGB image signals, which are outputted from the image sensor 51c, coincides with the set signal ratio r1:g1:b1 for the normal mode. In a case where the signal ratio among the RGB image signals coincides with the set signal ratio r1:g1:b1, the light source control signals VB1*, VG1*, VR1*, VSA1*, and VSB1*, which have been applied to the respective LEDs 20 to 24 to obtain the RGB image signals, are set as the specific light source control signals.

In a calibration sequence for the first special mode, the calibration light controller 200a is controlled to simultaneously turn on the three LEDs (the G-LED 21, the first special light LED 23, and the second special light LED 24).

The green light, the first special light, and the second special light from the respective LEDs 21, 23, and 24 are applied to the integrating sphere ST. The image sensor 51c images the integrating sphere ST under the light of the three colors, and outputs the RGB image signals. The image sensor 51c images the integrating sphere ST while the bit numbers of the light source control signals VG[m], VSA[m], and VSB[m], which are applied to the respective LEDs 21, 23, and 24, are changed in the manner similar to the calibration sequence for the normal mode.

The specific light source control signal setter 200b determines whether the signal ratio between the B and G image signals, of the RGB image signals outputted from the image sensor 51, coincides with the set signal ratio b2:g2 for the first special mode. In a case where the signal ratio between the B and G image signals coincides with the set signal ratio b2:g2, the light source control signals VG2*, VSA2*, and VSB2*, which have been applied to the respective LEDs 21, 23, and 24 to obtain the B and G image signals, are set as the specific light source control signals.

In a calibration sequence for the second special mode, the calibration light controller 200a is controlled to simultaneously turn on the four LEDs (G-LED 21, the R-LED 22, the first special light LED 23, and the second special light LED 24). The green light, the red light, the first special light, and the second special light from the respective LEDs are applied to the integrating sphere ST. The image sensor 51c images the integrating sphere ST under the light of these four colors, and outputs the RGB image signals. The image sensor 51c images the integrating sphere ST while the bit numbers of the light source control signals VG[m], VR[m], VSA[m], and VSB[m], which are applied to the respective LEDs 21 to 24, are changed in the manner similar to the calibration sequence of the normal mode.

The specific light source control signal setter 200b determines whether the signal ratio among the RGB image signals, which are outputted from the image sensor 51c, coincides with the set signal ratio r3:g3:b3 for the second special mode. In a case where the signal ratio among the RGB image signals coincides with the set signal ratio r3:g3:b3, the specific light source control signals VG3*, VR3*, VSA3*, and VSB3*, which have been applied to the respective LEDs 21 to 24 to obtain the RGB image signals, are set as the specific light source control signals.

In a calibration sequence for the third special mode, the calibration light controller 200a is controlled to simultaneously turn on the two LEDs (the second special light LED 24 and the third special light LED 25). The second special light and the third special light from the respective LEDs 24 and 25 are applied to the integrating sphere ST. The image sensor 51c images the integrating sphere ST under the light of these two colors, and outputs the RGB image signals. The image sensor 51c images the integrating sphere ST while the bit numbers of the light source control signals VSB[m] and VSC[m], which are applied to the respective LEDs 24 and 25, are changed in the manner similar to the calibration sequence for the normal mode.

The specific light source control signal setter 200b determines whether the signal ratio between the B and G image signals, of the RGB image signals outputted from the image sensor 51, coincides with the set signal ratio b4:g4 for the third special mode. In a case where the signal ratio between the B and G image signals coincides with the set signal ratio b4:g4, the specific light source control signals VSB4* and VSC4*, which have been applied to the respective LEDs 24 and 25 to obtain the B and G image signals, are set as the specific light source control signals.

The light control table generating unit 202 has a reference light source control signal setter 202a, a control signal ratio calculator 202b, a light source control signal setter 202c for the brightness step n (hereinafter simply referred to as the light source control signal setter 202c), and an associating section 202d. The light control table generating unit 202 follows a table generating sequence determined for each observation mode. In the table generating sequence for the normal mode, the reference light source control signal setter 202a compares the bit numbers of the specific light source control signals VB1*, VG1*, VR1*, VSA1*, and VSB1* with each other and determines the specific light source control signal with the largest bit number. For example, given that the specific light source control signal VB1* has the largest bit number, the light source control signal VB[m] of the B-LED 20 is set as the reference light source control signal. Then, the control signal ratio calculator 202b calculates the control signal ratio VG1*/VB1* of the specific light source control signal VG1* to the specific light source control signal VB1* and the control signal ratio VR1*/VB1* of the specific light source control signal VR1* to the specific light source control signal VB1*.

Figure 19:
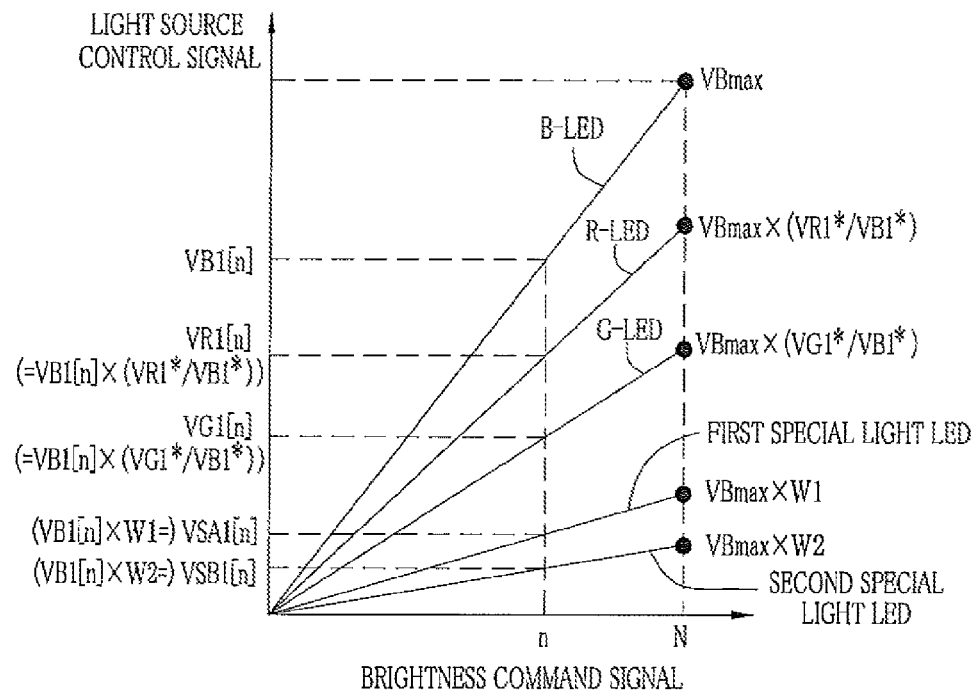
FIG. 19 is an explanatory view illustrating a method for setting a light source control signal for brightness step n in the normal mode.

Next, the light source control signal setter 202c divides the maximum bit number VBmax of the light source control signal (the reference light source control signal) VB[m] for the B-LED 20 by N. Thereby, a light source control signal VB1[n], which corresponds to the brightness step n, for the B-LED 20 is set (VB1[n]=n×VBmax/(N−1). Then, as shown in FIG. 19, the light source control signal VB1[n], which corresponds to the brightness step n, is multiplied by the control signal ratio VR1*/VB1*, and thereby a light source control signal VR1[n], which corresponds to the brightness step n, for the R-LED 22 is calculated. Furthermore, the light source control signal VB1[n], which corresponds to the brightness step n, is multiplied by the control signal ratio VG1*/VB1*, and thereby a light source control signal VG1[n], which corresponds to the brightness step n, for the G-LED 21 is calculated.

The light source control signal VB1[n], which corresponds to the brightness step n, is multiplied by W1 (a percentage between 0 to 100%), and thereby a light source control signal VSA1[n], which corresponds to the brightness step n, for the first special light LED 23 is calculated. The light source control signal VB1[n], which corresponds to the brightness step n, is multiplied by W2 (a percentage between 0 to 100%), and thereby a light source control signal VSB1[n], which corresponds to the brightness step n, for the second special light LED 24 is calculated.

The associating section 202d associates the light source control signal VB1[n], which corresponds to the brightness step n and is set by the light source control signal setter 202c for the brightness step n, with the brightness command signal n. Thereby the associating section 202d generates the B1 light control table. The associating section 202d associates each of the light source control signals VG1[n], VR1[n], VSA1[n], and VSB1[n], each corresponding to the brightness step n, with the brightness command signal n, in a manner similar to the B1 light control table. Thereby the associating section 202d generates the G1 light control table, the R1 light control table, the SA1 light control table, and the SB1 light control table. By controlling the light amounts of the LEDs 20 to 24 based on the five light control tables, respectively, the optimum white balance is maintained regardless of the value of the brightness command signal n.

In the table generating sequence for the first special mode, first, the reference light source control signal setter 202a compares the bit numbers of the specific light source control signals VG2*, VSA2*, and VSB2* with each other, and determines the specific light source control signal with the largest bit number. For example, given that the specific light source control signal VSA2* has the largest bit number, the reference light source control signal setter 202a sets the light source control signal VSA[m] (for the first special light LED 23) as the reference light source control signal. Then, the control signal ratio calculator 202b calculates the control signal ratio VG2*/VSA2* between the specific light source control signals VG2* and VSA2*.

Figure 20:
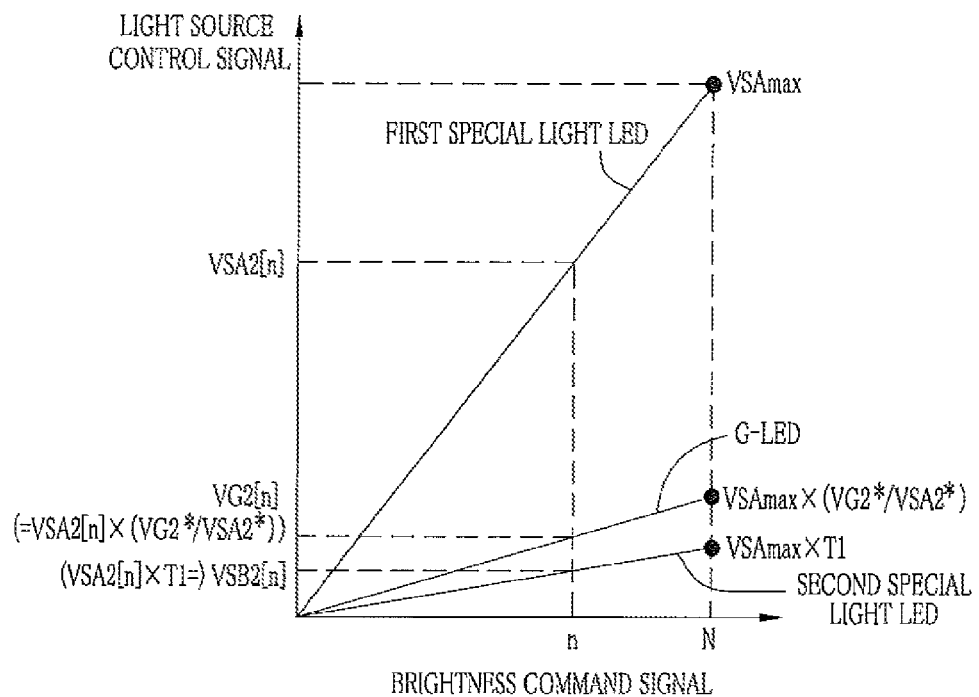
FIG. 20 is an explanatory view illustrating a method for setting a light source control signal for brightness step n in a first special mode.

Next, the light source control signal setter 202c divides the maximum bit number VSAmax of the light source control signal (the reference light source control signal) VSA[m] for the first special light LED 23 by N to set the light source control signal VSA2[n], which corresponds to the brightness step n, for the first special light LED 23 (VSA2[n]=n×VSAmax/(N−1)). Then, as shown in FIG. 20, the light source control signal VSA2[n], which corresponds to the brightness step n, is multiplied by the control signal ratio VG2*/VSA2*, and thereby the light source control signal VG2[n], which corresponds to the brightness step n, for the G-LED 21 is calculated. The light source control signal VSA2[n], which corresponds to the brightness step n, is multiplied by T1 (a percentage between 0 to 100%), and thereby the light source control signal VSB2[n], which corresponds to the brightness step n, for the second special light LED 24 is calculated.

The associating section 202d associates the light source control signal VG2[n], which corresponds to the brightness step n and is set by the light source control signal setter 202c, with the brightness command signal n, and thereby the G2 light control table is generated. The associating section 202d associates the light source control signal VSA2[n], which corresponds to the brightness step n, with the brightness command signal n and thereby generates the SA2 light control table, in a manner similar to the G2 light control table. The associating section 202d associates the light source control signal VSB2[n], which corresponds to the brightness step n, with the brightness command signal n and thereby generates the SB2 light control table, in a manner similar to the G2 light control table. By controlling the light amounts of the LEDs 21, 23, and 24 based on the three light control tables, respectively, the optimum white balance is maintained regardless of the value of the brightness command signal n.

In the table generating sequence for the second special mode, first, the reference light source control signal setter 202a compares the bit numbers of the specific light source control signals VG3*, VR3*, VSA3*, and VSB3* with each other, and determines the specific light source control signal with the largest bit number. For example, given that the specific light source control signal VSA3* has the largest bit number, the light source control signal VSA[m] for the first special light LED 23 is set as the reference light source control signal. The control signal ratio calculator 202b calculates the control signal ratios VG3*/VSA3*, between the specific light source control signals VG3* and VSA3*, and VR3*/VSA3*, between the specific light source control signals VR3* and VSA3*.

Figure 21:
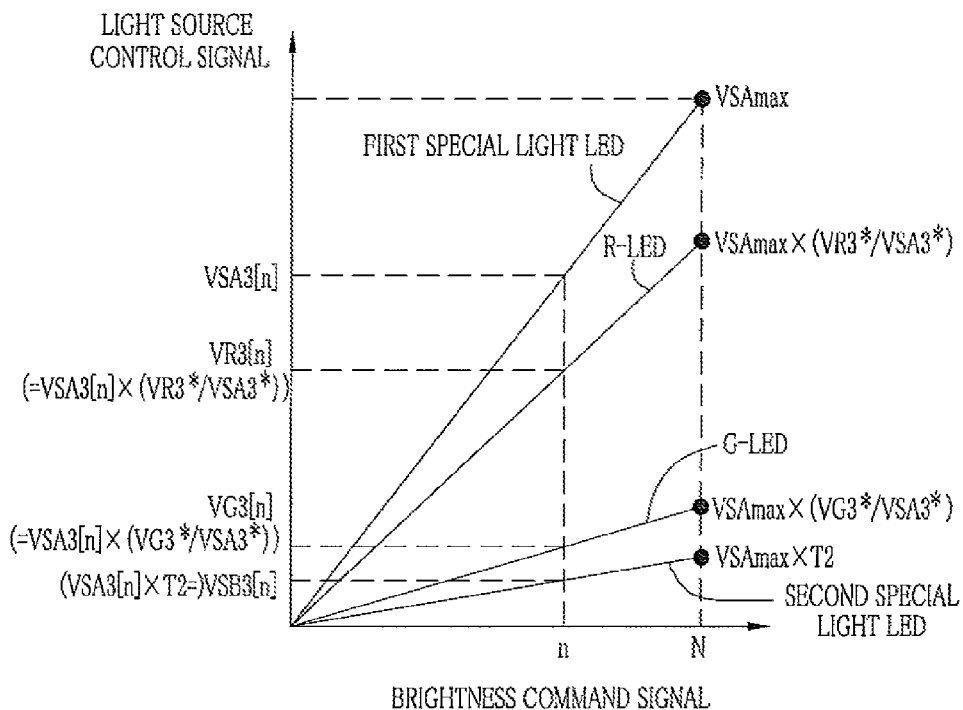
FIG. 21 is an explanatory view illustrating a method for setting a light source control signal for brightness step n in a second special mode.

Next, the light source control signal setter 202c divides the maximum bit number VSAmax of the light source control signal (the reference light source control signal) VSA[m] for the first special light LED 23 by N. Thereby the light source control signal setter 202c sets a light source control signal VSA3[n], which corresponds to the brightness step n, for the first special light LED 23 (VSA3[n]=n×VSAmax/(N−1)). Then, as shown in FIG. 21, the light source control signal VSA3[n], which corresponds to the brightness step n, is multiplied by the control signal ratio VR3*/VSA3*, and thereby a light source control signal VR3[n], which corresponds to the brightness step n, for the R-LED 22 is calculated. The light source control signal VSA3[n], which corresponds to the brightness step n, is multiplied by the control signal ratio VG3*/VSA3*, and thereby a light source control signal VG3[n], which corresponds to the brightness step n, for the G-LED 21 is calculated. Furthermore, the light source control signal VSA3[n], which corresponds to the brightness step n, is multiplied by T2 (a percentage between 0 to 100%), and thereby a light source control signal VSB3[n], which corresponds to the brightness step n, for the second special light LED 24 is calculated.

The associating section 202d associates the light source control signal VG3[n], which corresponds to the brightness step n and is set by the light source control signal setter 202c, with the brightness command signal n. Thereby the associating section 202d generates the G3 light control table. The associating section 202d associates the light source control signal VR3[n], which corresponds to the brightness step n, with the brightness command signal n, and thereby generates the R3 light control table. The associating section 202d associates the light source control signal VSA3[n], which corresponds to the brightness step n, with the brightness command signal n, and thereby generates the SA3 light control table. The associating section 202d associates the light source control signal VSB3[n], which corresponds to the brightness step n, with the brightness command signal n, and thereby generates the SB3 light control table. Thus, the R3 light control table, the SA3 light control table, and the SB3 light control table are generated in a manner similar to the G3 light control table. By controlling the light amounts of the LEDs 21 to 24 based on the four light control tables, respectively, the optimum white balance is maintained regardless of the value of the brightness command signal n.

In the table generating sequence for the third special mode, first, the reference light source control signal setter 202a compares the bit number of the specific light source control signal VSB4* with the bit number of the specific light source control signal VSC4*, and determines the greater of the two. For example, given that the specific light source control signal VSC4* is greater than the specific light source control signal VSB4*, the reference light source control signal setter 202a determines the light source control signal VSC[m] (for the third special light LED 25) as the reference light source control signal. The control signal ratio calculator 202b calculates the control signal ratio VSB4*/VSC4* between the specific light source control signal VSB4* and the reference light source control signal VSC4*.

Figure 22:
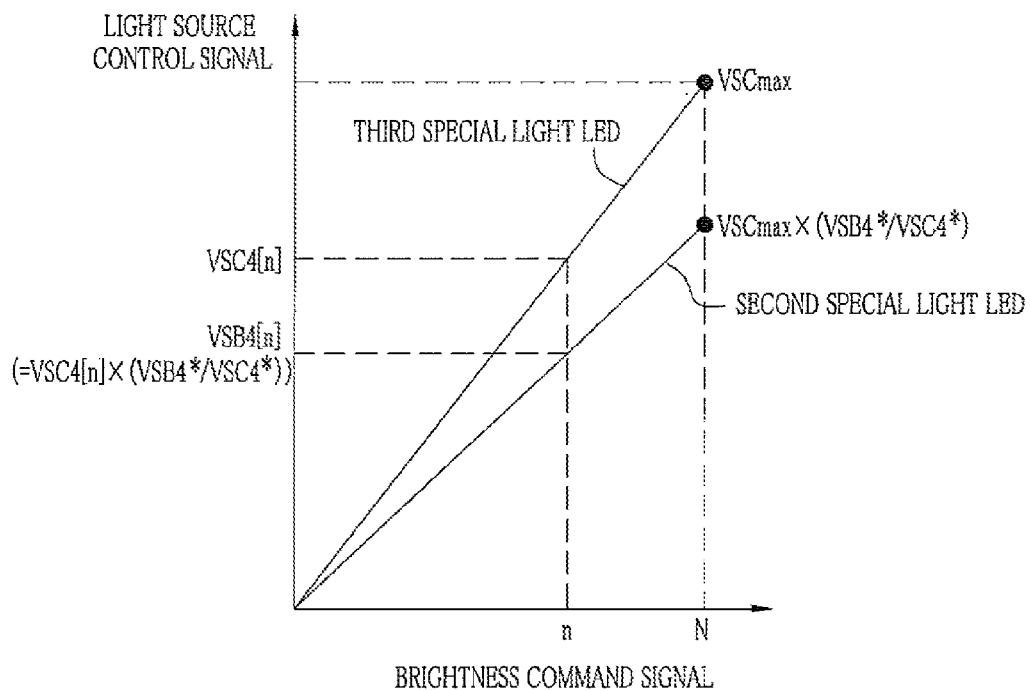
FIG. 22 is an explanatory view illustrating a method for setting a light source control signal for brightness step n in a third special mode.

Next, the light source control signal setter 202c divides the maximum bit number VSCmax of the light source control signal (the reference light source control signal) VSC[m] for the third special light LED 25 by N. Thereby, the light source control signal setter 202c sets a light source control signal VSC4[n], which corresponds to the brightness step n, for the third special light LED 25 (VSC4 [n]=n×VSCmax/(N−1)). Then, as shown in FIG. 22, the light source control signal VSC4[n], which corresponds to the brightness step n, is multiplied by the control signal ratio VSB4*/VSC4*, and thereby a light source control signal VSB4[n], which corresponds to the brightness step n, for the second special light LED 24 is calculated.

The associating section 202d associates the light source control signal VSB4[n], which corresponds to the brightness step n and is set by the light source control signal setter 202c, with the brightness command signal n. Thereby the associating section 202d generates the SB4 light control table. The associating section 202d associates the light source control signal VSC4[n], which corresponds to the brightness step n, with the brightness command signal n, in a manner similar to the SB4 light control table. Thereby the associating section 202d generates the SC4 light control table. By controlling the light amounts of the LEDs 24 and 25 based on the two light control tables (SB4 and SC4 light control tables), respectively, the optimum white balance is maintained regardless of the value of the brightness command signal n.

Note that, in the above embodiments, it is preferred to store the joint tables (for each observation mode) which are obtained in the calibration mode, in association with the scope ID (denoted as "ID" in FIG. 1) of the endoscope 12 or 100 in the memory 31 of the light source device 14. In a case where the calibrated endoscope 12 or 100 is connected to the light source device 14 and the processor device 16, an ID reader, which is denoted as "RD" in FIG. 1, reads out the scope ID of the endoscope 12 or 100, and then reads out the joint tables (for each observation mode) which correspond to the read scope ID.

Note that, in the above embodiments, the calibration of the present invention is applied to the endoscope having the color image sensor. The calibration of the present invention may be applied to a monochrome frame-sequential type endoscope.

Various changes and modifications are possible in the present invention and may be understood to be within the present invention.

What is claimed is:

1. A calibration method for an endoscope system having semiconductor light sources for emitting different types of illumination light with different wavelength ranges, a light source controller for controlling the semiconductor light sources with respective light source control signals, and a brightness command signal generator for generating a brightness command signal n for commanding the light source controller to change a light amount of the each illumination light based on a brightness step n (n being an integer from 0 to N−1) of N (N being an integer greater than or equal to 2) levels, a light amount ratio between the light amounts of the illumination light being set in advance as a set light amount ratio, the calibration method comprising the steps of:
(a) applying a first light source control signal to the each semiconductor light source and allowing the each semiconductor light source to emit the each illumination light to a reference object, and calculating a light amount of the illumination light reflected from the reference object with a light amount calculator;
(b) generating calibration data by associating the first light source control signals with the light amounts of the illumination light calculated by the light amount calculator in a case where the first light source control signals are applied;
(c) setting a maximum light amount of the each illumination light in accordance with the set light amount ratio and based on the calibration data;
(d) setting an nth light amount for the each illumination light based on the maximum light amount for the each illumination light, the nth light amount increasing or decreasing linearly relative to the brightness step n;
(e) referring to the calibration data and determining a light source control signal corresponding to the nth light amount from the first light source control signals, the determined light source control signal being set as a second light source control signal corresponding to the brightness step n; and
(f) associating the second light source control signal with a brightness control signal n for the brightness step n, and generating a light control table.

2. The calibration method according to claim 1, wherein the ratio of the light amount of specific illumination light is set to be the highest of the ratios of the light amounts of the different types of the illumination light, and
in the step (c), a highest light amount of the specific illumination light in the calibration data is set as the maximum light amount of the specific illumination light, and the maximum light amount of the illumination light other than the specific illumination light is set based on the maximum light amount of the specific illumination light and the set light amount ratio.

3. The calibration method according to claim 2, wherein the maximum light amount of the illumination light other than the specific illumination light is calculated by multiplying the maximum light amount of the specific illumination light by a control signal ratio for controlling the light amount relative to the light amount of the specific illumination light, and the control signal ratio is obtained based on the set light amount ratio.

4. The calibration method according to claim 1, wherein, in the step (d), the nth light amount of the each illumination light, corresponding to the brightness step n, is obtained based on a value calculated by dividing the maximum light amount of the each illumination light by N.

5. The calibration method according to claim 1, further comprising the steps of:
(g) controlling the emission of the each semiconductor light source based on the light control table and illuminating the reference object with the each illumination light, and calculating the light amount of the each illumination light reflected from the reference object with a light amount calculator:
(h) calculating an error between the each light amount corresponding to the brightness step n, calculated in the step (g), and a target light amount of the each illumination light;
(i) determining whether the error is within a predetermined range or not, and not regenerating the light control table in a case where the error is within the predetermined range and regenerating the light control table in a case where the error is out of the predetermined range.

6. The calibration method according to claim 5, wherein the step (i) includes the steps of:
(i1) resetting the light amount of the each illumination light in accordance with the set light amount ratio and based on the light amount of the illumination light with the largest error, in the case where the error is out of the predetermined range;
(i2) calculating an error between a light amount of the each illumination light after resetting and the target light amount of the each illumination light;
(i3) selecting the light amount of the illumination light with the smaller of the errors calculated in the step (h) or the step (i2); and
(i4) referring to the calibration data and determining a third light source control signal, which corresponds to the light amount of the illumination light selected in the step (i3), from the first light source control signals, and re-associating the determined third light source control signal with the brightness command signal n that corresponds to the brightness step n in the light control table.

7. The calibration method according to claim 1, further comprising the step of:
generating a joint table by joining a control signal correction table, in which the second light source control signal is associated with a linear-change light source control signal for linearly increasing or decreasing the light amount of the each illumination light, and the light control table.

8. The calibration method according to claim 1, wherein the semiconductor light sources have an R-LED for emitting red light, a G-LED for emitting green light, and a B-LED for emitting blue light.

9. The calibration method according to claim 8, wherein the semiconductor light sources have special light LEDs at least including a first special light LED and a second special light LED, and the first special light LED emits first special light having a first wavelength range, and the second special light LED emits second special light having a second wavelength range, and the first and second wavelength ranges differ from wavelength ranges of the red light, the green light, and the blue light.

10. The calibration method according to claim 9, wherein the endoscope system has a normal mode, in which at least the R-LED, the G-LED, and the B-LED are turned on to emit white light, and a special mode, in which at least the first and second special light LEDs are turned on to emit special light, and
at least the steps (c), (d), (e), and (f) are performed in the each observation mode to generate the light control tables which differ between the normal and the special modes.

11. The endoscope system according to claim 1, further comprising:
a storage unit in which a scope ID of an endoscope is associated with the light control table and stored; and
an ID reader for reading out the scope ID of the endoscope.

12. An endoscope system having semiconductor light sources for emitting different types of illumination light with different wavelength ranges, a light source controller for controlling the semiconductor light sources with respective light source control signals, and a brightness command signal generator for generating a brightness command signal n for commanding the light source controller to change a light amount of the each illumination light based on a brightness step n (n being an integer from 0 to N−1) of N (N being an integer greater than or equal to 2) levels, a light amount ratio between the light amounts of the illumination light being set in advance as a set light amount ratio, the endoscope system comprising:
a calibration light controller for applying a first light source control signal to the each semiconductor light source and allowing the each semiconductor light source to emit the each illumination light to a reference object;
a light amount calculator for calculating a light amount of the each illumination light reflected from the reference object;
a first associating section for generating calibration data by associating the first light source control signals with the light amounts of the illumination light calculated by the light amount calculator in a case where the first light source control signals are applied;
a maximum light amount setter for setting a maximum light amount of the each illumination light in accordance with the set light amount ratio and based on the calibration data;
an nth light amount setter for setting an nth light amount for the each illumination light based on the maximum light amount of the each illumination light, the nth light amount increasing or decreasing linearly relative to the brightness step n;

a light source control signal setter for referring to the calibration data and determining a light source control signal corresponding to the nth light amount from the first light source control signals, and setting the determined light source control signal as a second light source control signal corresponding to the brightness step n; and
a second associating section for associating the second light source control signal with the brightness command signal n corresponding to the brightness step n, to generate a light control table.

13. A calibration method for an endoscope system having semiconductor light sources for emitting different types of illumination light with different wavelength ranges, a light source controller for controlling the semiconductor light sources with respective light source control signals, a brightness command signal generator for generating a brightness command signal n for commanding the light source controller to change a light amount of the each illumination light based on a brightness step n (n being an integer from 0 to N−1) of N (N being an integer greater than or equal to 2) levels, and a color image sensor, a signal ratio between image signals of different colors being set in advance as a set signal ratio, the image signals being obtained by imaging an observation object under the different types of the illumination light with the color image sensor, the calibration method comprising the steps of:
(A) applying a light source control signal to the each semiconductor light source and allowing the each semiconductor light source to emit the each illumination light to a reference object, and imaging the reference object with the color image sensor;
(B) setting the light source control signal which makes the signal ratio between image signals of different colors obtained by imaging the reference object and outputted from the color image sensor equivalent to the set signal ratio, as a specific light source control signal;
(C) setting the light source control signal which is applied to the semiconductor light source with high light emission, as a reference light source control signal, the highest of the specific light source control signals being applied to the semiconductor light source with the high light emission;
(D) obtaining a control signal ratio between the specific light source control signals;
(E) obtaining the light source control signal for the brightness step n for the each semiconductor light source based on the reference light source control signal and the control signal ratio, the light source control signal for the brightness step n corresponding to the brightness step n; and
(F) storing the light source control signal for the brightness step n and the brightness command signal n for the brightness step n in a light control table such that the light source control signal for the brightness step n is associated with the brightness command signal n for the brightness step n.

14. The calibration method according to claim 13, wherein, in the step (E), the light source control signal for the brightness step n, for the semiconductor light source with the high light emission, is calculated by dividing the reference light source control signal by N, and the light source control signal for the brightness step n, for the semiconductor light source other than the high-emission semiconductor light source, is calculated by multiplying the reference light source control signal by the control signal ratio.

* * * * *